(12) United States Patent
Ron et al.

(10) Patent No.: US 7,008,628 B2
(45) Date of Patent: Mar. 7, 2006

(54) END MODIFIED THERMAL RESPONSIVE HYDROGELS

(75) Inventors: Eyal S. Ron, Lexington, MA (US); Lev Bromberg, Swampscott, MA (US); Marina Temchenko, Swampscott, MA (US)

(73) Assignee: Madasa LLC, Lexington, MA (US)

( * ) Notice: Subject to any disclaimer, the term of this patent is extended or adjusted under 35 U.S.C. 154(b) by 343 days.

(21) Appl. No.: 10/007,184

(22) Filed: Nov. 13, 2001

(65) Prior Publication Data

US 2003/0092776 A1 May 15, 2003

Related U.S. Application Data

(63) Continuation of application No. 09/368,440, filed on Aug. 4, 1999, now Pat. No. 6,316,011.

(60) Provisional application No. 60/095,330, filed on Aug. 4, 1998, provisional application No. 60/097,741, filed on Aug. 24, 1998.

(51) Int. Cl.
*A61K 6/00* (2006.01)
*A61K 7/00* (2006.01)

(52) U.S. Cl. ............... 424/401; 424/78.02; 424/78.03; 424/78.18

(58) Field of Classification Search ............... 424/400, 424/401, 78.02, 78.03, 78.08, 78.19, 78.18, 424/78.31, 40, 443, 450, 489, 59
See application file for complete search history.

(56) References Cited

U.S. PATENT DOCUMENTS

| | | | |
|---|---|---|---|
| 4,474,752 A | | 10/1984 | Haslam et al. |
| 5,252,318 A | | 10/1993 | Joshi et al. |
| 5,292,516 A | * | 3/1994 | Viegas et al. ............... 424/423 |
| 5,548,035 A | | 8/1996 | Kim et al. |
| 5,599,534 A | | 2/1997 | Himmelstein |
| 5,702,717 A | | 12/1997 | Cha et al. |
| 5,939,485 A | * | 8/1999 | Bromberg et al. .......... 524/556 |
| 6,316,011 B1 | * | 11/2001 | Ron et al. .................. 424/401 |

FOREIGN PATENT DOCUMENTS

| | | | |
|---|---|---|---|
| EP | 0 583 814 | | 2/1994 |
| JP | 07-018042 | | 1/1995 |
| WO | WO95/24430 | * | 9/1995 |
| WO | WO 97/00275 | | 1/1997 |

OTHER PUBLICATIONS

Bromberg et al., "Temperature-Responsive Gels and Thermogelling Polymer Matrices for Protein and Peptide Delivery" Avd. Drug Deliv. Rev. 31:197 (1998).
Bromberg, Lev "Scaling of Rheological Properties of Hydrogels from Associating Polymers" Macromolecules 31:6148 (Sep. 1998).
Bromberg, Lev "Self-Assembly in Aqueous Solutions of Polyether-Modified Poly(acrylic acid)" Langmuir 14:5806 (Sep. 1998).
Bromberg, Lev "Polyether-Modified Poly(acrylic acid): Synthesis and Applications" Ind. Eng. Chem. Res. 37:4267 (Sep. 1998).
Bromberg, Lev "Aggregation Phenomena in Aqueous Solutions of Hydrophobically Modified Polyelectrolytes. A Probe Solubilization Study." Macromolecules 32:3649 (Apr. 1999).
Huibers, et al. "Reversible Gelation in Semidilute Aqueous Solutions of Associative Polymers: A Small-Angle Neutron Scattering Study" Macromolecules 32:4889 (Jun. 1999).
Shultz et al. "Synthesis and Characterization of Hydrophobically Associating Water-Soluble Polymers" Macromolecular Complexes in Chemistry and Biology, Ed. Dubin/Bock/Davis/S.

* cited by examiner

*Primary Examiner*—Dameron L. Jones

(57) ABSTRACT

A pharmaceutic composition includes a pharmaceutically acceptable carrier, comprising a reverse thermally viscosifying polymer. The polymer includes a linear block copolymer, wherein at least one block comprises a poloxamer; and at least one block comprises a biocompatible polymer or oligomer, in an aqueous medium. The composition also includes an active agent which imparts a pharmaceutic or cosmetic effect. The composition viscosifies in response to an environmental stimulus. The composition is suitable for administration of the pharmaceutical agent across dermal, otic, rectal, vaginal, ophthalmic, esophageal and nasal mucosal membranes.

29 Claims, 6 Drawing Sheets

END MODIFIED THERMAL RESPONSIVE HYDROGELS

This application is a continuation application of U.S. Ser. No. 09/368,440; now U.S. Pat. No. 6,316,011, filed Aug. 4, 1999, which is a continuation in part application of and which claims priority from U.S. Ser. No. 60/095,330 filed Aug. 4, 1998 and U.S. Ser. No. 60/097,741 filed Aug. 24, 1998.

BACKGROUND OF THE INVENTION

The present invention relates to polymers and compositions useful in a variety of pharmaceutical and personal care products and applications, and in particular, compositions useful topical and/or mucosal applications, such as esophageal, otic, vaginal, rectal, ophthalmic and treatments of disorders and imperfections of the skin.

One of the major concerns in the delivery of drugs is the bioavailability of the drug. Depending upon the nature of the drug and the route of delivery, the bioavailability may be very low due to, for example, the degradation of oral-delivered drugs by hepato-gastrointestinal first-pass elimination or rapid clearance of the drug from the site of application. The net result is that frequent dosing may be required with higher than needed amounts of drug, which can lead to undesired side effects. Thus, it is desired by the pharmaceutical industry to have ways of administering drugs such that their availability can be controlled in an even dosing manner, the amounts of drugs can be kept as low as possible to minimize side effects, and dosing regime can be kept to a minimum to provide greater convenience to the subject, thus promoting greater compliance with appropriate dosing.

The mucosal tissue is an ideal site for drugs to be delivered locally and systemically because these tissues are exposed to an abundant blood supply. In addition, drug transport is aided by the fact that diffusion equilibria are not approached. Also, mucosal tissues have a very thin epithelium with minimal keratinized tissue that does not hinder the drug transport as compared to normal epidermal skin containing thick layers of keratinized tissues. Therefore, mucosal tissues offer an attractive surface to promote drug absorption.

Despite the advantages of mucosal tissue as a site for drug delivery, direct topical application of pharmacological agents onto mucosal tissues has very limited value, due to the facile clearance of those agents via washing or rubbing. The difficulty in the administration of such systems is the necessity for the drugs to remain in contact with the target tissue for a sufficient period of time to provide sufficient amount of drug to achieve the desired therapeutic effect. In addition to protection from pH, enzymatic attack and physiological removal by swallowing, the system needs to provide a long-term delivery to enhance the therapeutic profile (Guo, J-H; "Bioadhesive Polymer Buccal Patches for Buprenorphine Controlled Delivery: Formulation, In-vitro Adhesion and Release Properties", *Drug Dev. Ind. Pharm.*, 20(18), 2809, 1994; McQuinn, R. L.; et al; "Sustained Oral Mucosal Delivery in Human Volunteers of Buprenorphine from a Thin Non-eroding Mucoadhesive Polymeric Disc", *J. Control Rel.* 34, 243, 1995). Hence, specific formulations having improved bioadhesion designed to prolong the availability of the therapeutic product on the surface and to enable sustained release of the active ingredient are desired.

Bioadhesion or mucoadhesion is generally understood as the ability of a biological or synthetic material to "stick" to mucous membrane, resulting in adherence of the material to the tissue for protracted period of time. This concept has received significant attention because of enhanced drug bioavailability due to the increased amount of time in which the bioadhesive dosage form is in contact with the targeted tissue, as compared to a standard dosage form. In order for the material to be bioadhesive, it must interact with mucous which is a highly hydrated, viscous anionic hydrogel layer protecting the mucosa.

Many instances are known in the pharmaceutic industry where it is desired to have certain properties of viscosity in order to facilitate the objectives noted above. Hydrogels, such as cellulosics, have been included as thickeners in pharmaceutic compositions. A hydrogel is a polymer composition, in which the polymer forms a network swollen in water that is sufficiently stabilized either by covalent bonding or by physical bonding (hydrogen, ionic, hydrophobic, or van der Waals interactions). The hydrophilic areas of the polymer chain absorb water and form a gel region. The extent of gelation depends upon the volume of the solution which the gel region occupies.

Reversibly gelling solutions are known in which the solution viscosity increases and decreases with an increase and decrease in temperature, respectively. Such reversibly gelling systems are useful wherever it is desirable to handle a material in a fluid state, but performance is preferably in a gelled or more viscous state.

A known material with these properties is a thermal setting gel using poly(ethyleneoxide)/poly(propyleneoxide) block copolymers available commercially as Pluronic® poloxamers (BASF, Ludwigshafen, Germany) and generically known as poloxamers. See. U.S. Pat. Nos. 4,188,373, 4,478,822 and 4,474,751. Adjusting the temperature of the polymer gives the desired liquid-gel transition. However, concentrations of the poloxamer polymer of at least 18–20% by weight are needed to produce a composition which exhibits such a transition at commercially or physiologically useful temperatures. Also, solutions containing 18–20% by weight of responsive polymer are typically very viscous even in the "liquid" phase, so that these solutions can not function under conditions where low viscosity, free-flowing is required prior to transition. In addition, these polymer concentrations are so high that the material itself may cause unfavorable physiological interactions during use.

Another known system which is liquid at room temperature, but forms a semi-solid when warmed to about body temperature is formed from tetrafunctional block polymers of polyoxyethylene and polyoxypropylene condensed with ethylenediamine, commercially available as Tetronic® poloxamers. These compositions are formed from approximately 10% to 50% by weight of the poloxamer in an aqueous medium. See, U.S. Pat. No. 5,252,318. Although Pluronic®- and Tetronic®-based block copolymers exhibit reversible viscosification, they did not offer any bioadhesion properties.

Various attempts have been made with limited success to combine the properties of a thermally gelling polymer and a bioadhesive polymer.

Himmelstein in U.S. Pat. No. 5,599,534 described the combination of a carboxylic acid-containing polymer such as poly(acrylic acid) with alkyl cellulose derivatives such as hydroxypropylmethylcellulose. Yet, the system required a pH shift in order to observe gelation.

Joshi et al. in U.S. Pat. No. 5,252,318 reports reversible gelling compositions which are made up of a physical blend of a pH-sensitive gelling polymer (such as a cross-linked poly(acrylic acid) and a temperature-sensitive gelling polymer (such as methyl cellulose or block copolymers of poly(ethyleneoxide) and poly(propyleneoxide)). In compositions including methylcellulose, 5- to 8-fold increases in viscosity are observed upon a simultaneous change in temperature and pH for very low methylcellulose levels (1–4% by weight). See, FIGS. 1 and 2 of Joshi et al. In compositions including Pluronic® and Tetronic® poloxamers, significant increases in viscosity (5- to 8-fold) upon a simultaneous change in temperature and pH are observed only at much higher polymer levels. See, FIGS. 3–6 of Joshi et al.

Hoffman et al. in WO 95/24430 and D. Hourdet, F. L'alloret, A. Durand, F. Lafuma, R. Audebert, and J-P. Cotton, Small-Angle Neutron Scattering Study of Microphase Separation in Thermoassociative Copolymers, *Macromolecules*, 31(16): 5323–5335, 1998, incorporated herein by reference, disclose block and graft copolymers comprising a poly(acrylic acid) component and a temperature-sensitive polymer component. The block and graft copolymers are well-ordered and contain temperature- or salt-sensitive polymer grafts bonded to the poly(acrylic acid) backbone. The copolymers are described as having a lower critical solution temperature (LCST), at which both sol-gel transition and visible or microphase separation occur. Thus, the gelation is accompanied by the clouding and opacification of the solution. (Hourdet's polymers do not opacify). Light transmission is reduced, which may be undesirable in many applications, where the aesthetic characteristics of the composition are of some concern.

Bromberg et al. in "Responsive Polymer Networks and Methods of Their Use" (WO 97/00275); in "A novel family of thermogelling materials of poly(ethylene oxide)-b-poly(propylene oxide)-b-poly(ethylene oxide) randomly grafted to poly(acrylic acid)," *J. Phys. Chem. B*, 102(11):1956–1963 (1998); in "Self-assembly in aqueous solutions of polyether-modified poly(acrylic acid)," *Langmuir*, 14(20):5806–5812 (1998); and in "Properties of aqueous solutions and gels of poly(ethylene oxide)-b-poly(propylene oxide)-b-poly(ethylene oxide)-g-poly(acrylic acid)," *J. Phys. Chem B*, 102(52):10736–10744 (1998); incorporated herein by reference, describe a graft-comb copolymer system where the poly(acrylic acid) serves as a backbone and the poloxamer was attached to the backbone through their poly(propylene oxide) moieties. This hydrogel system has a reduced stability due to the initial oxidation of the Pluronic® polymer. Also, by hindering access to the poly(acrylic) backbone bioadhesivity of the system is reduced.

Thus, the known systems which exhibit reversible gelation are limited in that they require large solids content and/or in that the increase in viscosity less desired. In addition, some known systems exhibit an increase in viscosity which is accompanied with the undesirable opacification of the composite. Other systems do not exhibit the desired bioadhesion properties or the stability required for quality pharmaceutical products.

It is the object of the present invention to overcome these and other limitations of the prior art.

SUMMARY OF THE INVENTION

The present invention provides compositions which possess improved flow and gelation characteristics. The composition is composed of biocompatible building blocks and includes a component capable of reversible gelation or viscosification. The composition demonstrates excellent bioadhesion and is useful in drug delivery applications.

The composition comprises a linear block copolymer including a polyoxyalkylene, such as poloxamer, end-modified by bioadhesive polymer, which may be poly(acrylic acid), or PAA, in an aqueous-based medium. The polymer is capable of aggregating in response to an increase in temperature.

In one aspect of the invention, the composition is capable of gelation or viscosification at very low solids content. In another aspect, the invention farther provides compositions having a minimum solids content which are capable of sustained delivery of an active agent. The composition incorporates poloxamer:poly(acrylic acid) polymer as a carrier.

The present invention overcomes the limitations of the prior art by providing compositions that includes a linear block copolymer capable of bioadhesion and reversible gelation or viscosification upon exposure to the appropriate environmental stimulus.

The present invention further provides a composition for use in pharmaceutic or cosmetic formulations as a surfactant or emulsifier in the solubilization of additives and, in particular, hydrophobic additives, or as a stabilizer to provide stable emulsions at elevated temperatures, or as a suspension agent for otherwise insoluble additives.

New ways of delivering drugs at the right time, in a controlled manner, with minimal side effects, and greater efficacy per dose are continually sought by the drug delivery and pharmaceutical industries. The reversibly gelling polymer of this invention has the physico-chemical characteristics that make it a suitable delivery vehicle for conventional small chemical drugs as well as new macromolecular (e.g., peptides) drugs or therapeutic products. It is particularly well-suited for transmucosal delivery.

These and other aspects of the invention are described.

The reversibly gelling composition comprises a linear copolymer including a polyoxyalkylene component having a hydrophobic region and a hydrophilic region capable of aggregation in response to an environmental stimulus. The polyoxyalkylene is modified at each end by a polymer component to form a linear block copolymer. The polymer component is biocompatible and is selected to increase the molecular weight of the composition. The polymer component does not interfere with the aggregation properties of the polyoxyalkylene.

In a preferred embodiment of the invention, the polymer component possesses bioadhesive or mucoadhesive properties. In a particularly preferred embodiment of the invention, the polymer component includes a poly(vinylcarboxylic acid), such as poly(acrylic acid) and poly(methacrylic acid), and the like. In a preferred embodiment, the polyoxyalkylene comprises a poloxamer.

In another aspect of the invention, a pharmaceutical composition is provided which includes the reversibly gelling block copolymer of the invention and a pharmaceutic agent selected to provide a preselected pharmaceutic effect. A pharmaceutic effect is one which seeks to treat the source or symptom of a disease or physical disorder. Pharmaceutics include those products subject to regulation under the FDA pharmaceutic guidelines, as well as consumer products. In addition, the composition may include agents promote bodily attractiveness or masking the physical manifestations of a disorder or disease, in lieu or in addition to the treatment of a physical disorder. The same agent may have either a cosmetic or pharmaceutical effect, depending upon the amounts used and the manner of administration.

The block copolymer and pharmaceutical compositions of the invention exhibit many advantages. Due to the gelling effect at physiologically appropriate conditions, they possesses the appropriate thickness, emolliency and cosmetic effect with a minimum of solids content. Furthermore, as is described hereinbelow, the linear block copolymer composition may be useful as a suspending agent for otherwise insoluble additives. Additionally, the block copolymer and pharmaceutical compositions of the invention are capable of solubilizing emulsions at elevated temperatures.

In another aspect of the invention, the polyoxyalkylene: poly(acrylic acid) polymer is incorporated into a composition to stabilize and solubilize hydrophobic agents The composition may be included to increase emulsion stability. Many emulsions, i.e., suspension of small droplets or particles of a first material in a second material, lose viscosity upon heating. The polyoxyalkylene:poly(acrylic acid) block copolymer composition retains its emulsifying properties even with temperature increase.

By "polyoxyalkylene" as that term is used herein, it is meant an oligomer or polymer of an oxyalkylene, or —O(CH$_2$)$_n$—, group, where n is in the range of 1 to 10 and where any H may be substituted for a linear or branched alkyl group. In preferred embodiments, n is 2 or 3, and is either unsubstituted or substituted by methyl group. The polyoxyalkylene component of the polymer possesses regions of hydrophobic character, e.g., poly(oxypropylene) blocks, and hydrophilic character, e.g., poly(oxyethylene) blocks in order to facilitate aggregation.

By "gelation" or "viscosification" as those terms are used herein, it is meant a drastic increase in the viscosity of the polymer solution. Gelation is dependent on the initial viscosity of the solution, but typically a viscosity increase at pH 7 and 1 wt % polymer concentration is in the range of preferably 2- to 100-fold, and preferably 5- to 50-fold, and more preferably 10- to 20-fold for a composition which is used in the preparation of the compositions of the invention. Such effects are observed in a simple polymeric solution and the effect may be modified by the presence of other components in the final composition.

By "reversibly gelling" as that term is used herein, it is meant that the process of gelation takes place upon an increase in temperature rather than a decrease in temperature. This is counter-intuitive, since solution viscosity typically decreases with an increase in temperature.

By "end-modified", as that term is used herein, it is meant that the polyoxyalkylene component is modified at its termini by chemical conversion and/or addition to the component. This in contrast to modifications which may occur along the backbone of the polyoxyalkylene.

By "use conditions" as that term is used herein it is meant all conditions to which the composition is likely to be exposed during its use, including during shipment and storage as well as during medical treatment or personal care.

The novel interaction between the constituent polymers components of the reversibly gelling composition permits formation of gels at very low solids content. Gelation and/or viscosification is observed in aqueous solutions having about 0.01 to 20 wt % of the polyoxyalkylene component and about 0.01 to 20 wt % of the end-modifying polymer component. A typical reversibly gelling composition may be comprised of about 0.01 wt % to about 1 to 8 wt %, preferably less than about 4 wt % of total polymer solids (e.g., polyoxyalkylene and biocompatible polymer), and more preferably less than 1 wt % total polymer solids, while still exhibiting reverse thermal viscosification. Of course, the total solids content of the composition, including additives and the pharmaceutic agent, may be much higher.

The relative proportion of polyoxyalkylene polymer and end-modifying polymer may vary in the composition, dependent upon the desired properties of the composition. Exemplary polymer compositions range from about 1:10 to about 10:1 polyoxyalkylene polymer:bioadhesive polymer. In one embodiment, the polyoxyalkylene component is present in a range of about 1 to 20 wt % and the end-modifying polymer is present in a range about of 99 to 80 wt %. In another embodiment, the polyoxyalkylene polymer component is present in a range of about 21 to 40 wt % and the polymer component is present in a range of about 79 to 60 wt %. In another embodiment, the polyoxyalkylene polymer component is present in a range of about 41 to 50 wt % and the polymer component is present in a range of about 59 to 50 wt %. In another embodiment, the polyoxyalkylene polymer component is present in a range of about 51 to 60 wt % and the polymer component is present in a range of about 49 to 40 wt %. In yet another embodiment, the polyoxyalkylene polymer component is present in a range of about 61 to 90 wt % and the polymer component is present in a range of about 39 to 20 wt %. In another embodiment, the polyoxyalkylene polymer component is present in a range of about 81 to 99 wt % and the polymer component is present in a range of about 19 to 1 wt %. A 50:50 mixture of poloxamer and poly(acrylic acid) has been demonstrated to provide the desired thermoviscosifying effect under most circumstances.

The reversibly gelling polymer described above may be included in a composition as a delivery vehicle for an active agent. In addition, the reversibly gelling composition may be included to improve the flow characteristics, thickness and other properties of the composition.

In one aspect of the invention, the reversibly gelling composition is incorporated into a composition to impart thickening properties to the composition at the use and/or application temperature. Such thickening properties include enhanced overall viscosity, as well as a desirable viscosity response with temperature. The composition may be useful as a thickener in pH ranges where other thickeners are not effective.

In another aspect of the invention, the reversibly gelling composition is incorporated into a composition to stabilize and solubilize hydrophobic agents in the composition. The reversibly gelling composition may be included to increase emulsion stability. Many emulsions (a suspension of small droplets or particles of a first material in a second material) lose viscosity upon heating. The reversibly gelling composition retains its emulsifying properties even at elevated temperatures.

In addition, the reversibly gelling composition may be included in the composition to impart emolliency to the composition. The composition may also act as a film-forming agent after it has been applied to the skin or other mucosal membrane. This film-forming agent may be used as a barrier to prevent water loss from the skin which contributes to the moisturization of the skin. The formed-film could also provide protective coating ("band-aid") to protect the tissue against environmental challenge(s) or to provide a mechanical separation between to adjust tissues (adhesion prevention).

In addition, it may be included in the composition to impart emollience to the composition. The composition may also act as a film-forming agent after it has been applied to the skin. This film-forming agent may be used as a barrier to prevent water loss from the skin which contributes to the moisturization of the skin.

BRIEF DESCRIPTION OF THE DRAWING

The invention is described with reference to the Drawing, which is presented for the purpose of illustration and is in no way intended to be limiting, and in which.

DETAILED DESCRIPTION OF THE INVENTION

Figure 1:
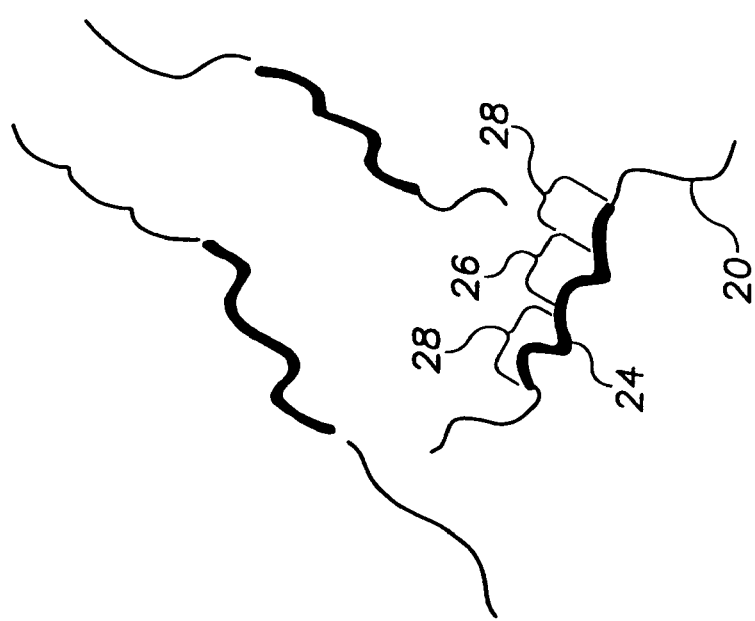
FIG. 1 is a schematic illustration of the poloxamer:poly (acrylic acid) polymer below and above the transition temperature illustrating the aggregation of the hydrophobic poloxamer regions.
Figure 1:
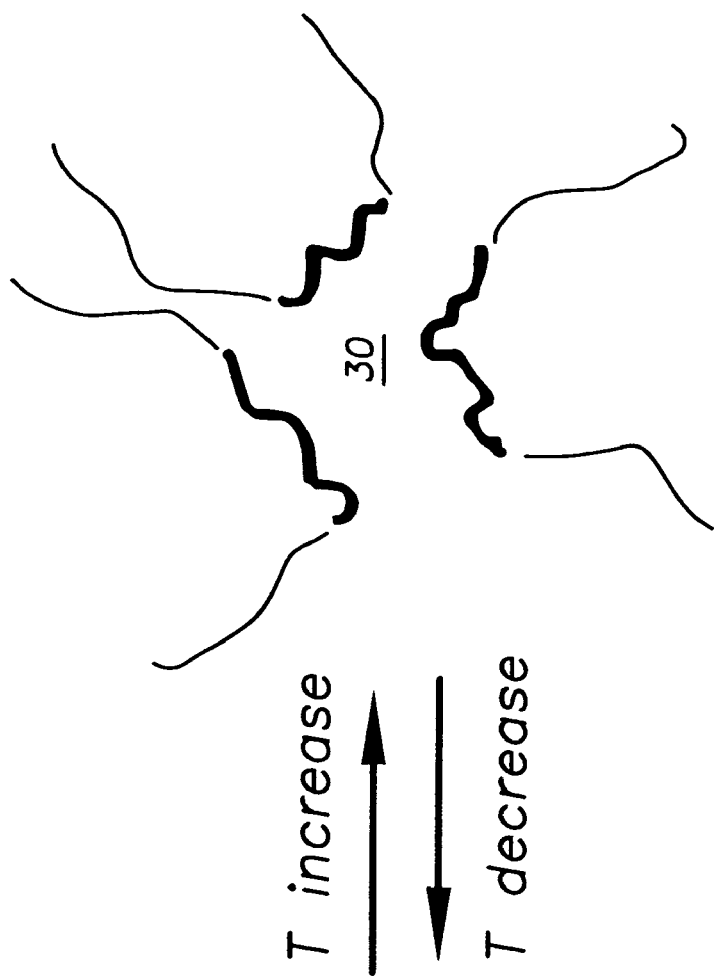

The present invention is directed to a composition comprising a polyoxyalkylene component that is end-modified with a biocompatible polymer to provide a linear copolymer. The polyoxyalkylene may be a thermogelling polymers, such as Pluronics® (BASF, Ludwigshafen, Germany) capped by both ends by oligomer of a mucoadhesive or bioadhesive polymer. The end-modified polyoxyalkylene compositions of the invention exhibit a reversible gelation at body temperature (25–40° C.) and/or at physiological pH (ca. pH 3.0–9.0) and even in basic environments up to pH 13 (e.g., the gastrointestinal environment) are particularly preferred for pharmaceutic and personal care applications. The end-modified polyoxyalkylene polymer functions as an environmentally sensitive thickening agent, and in addition possesses surfactant and emulsifying capabilities which may be beneficial in a pharmaceutic or personal care composition.

End-modified polyoxyalkylene block copolymer solutions at appropriate pH exhibit flow properties of a liquid at about room temperature, yet rapidly thickens into a gel consistency of at least about five times greater, preferably at least about 10 times greater, and even more preferably at least about 30 times and up to 100 times greater, viscosity upon increase in temperature of about 10 C and preferably about 5 C. The reversibly gelling composition of the present invention exhibit gelation even at very low polymer concentrations.

The polyoxyalkylene component contains a hydrophilic region and a hydrophobic region which makes it able to change its degree of association and/or agglomeration in response to an environmental stimulus. The stimulus most commonly is temperature, pH, ionic concentration, or solvent concentration, but other stimuli are within the scope of the invention if they cause the poloxamer to aggregate. Temperature is a preferred environmental trigger. The aggregation may be in the form of micelle formation, precipitation, labile crosslinking or other factors.

Exemplary polyoxyalkylenes are block copolymers of polyoxyethylene and polyoxypropylene having the general formula of a triad ABA block copolymer, b(EO) a(PO)b(EO) a, where EO=ethylene oxide and PO=propylene oxide moieties. Pluronic® (BASF) triblock polymers are commercially available for a in the range of 6 to 140 and b ranging from 6–100. Preferred embodiments include Pluronic® (BASF) triblock polymers for a in the range of 16 to 48 and b ranging from 54–62.

Other exemplary polyoxyalkylene polymers include alkyl poloxamers, which are a product of alcohol condensation reactions with a terminal alkyl or arylalkyl group. The alkyl group should have hydrophobic character, such as butyl, hexyl and the like. An alkyl poloxamer may have the general formula R—(OCH$_2$CH)$_n$OH, where R is a nonpolar pendant group such as alkyl and arylalkyl and the like, and n is in the range of 5–1000. A preferred alkylpoloxamer is polyethyleneglycol mono(nonylphenyl)ether.

One or more polyoxyalkylene components may be used in the reversibly gelling composition of the present invention.

In still other embodiments, the polyoxyalkylene component may additionally include cellulosic, cellulose ethers and guar gums which possess hydrophobic and hydrophilic regions along the polymer backbone which permit aggregation behavior.

The end-modification is achieved by oligomers or polymers which serves as an extension for the polyoxyalkylene poloxamer so that a multi-component composition is formed. This results in an extended linear polymer. The end-modifying polymer component increases the molecular weight of the composition, which amplifies the viscosification response. In addition, the polymer component may be a bioadhesive or mucoadhesive.

Suitable end-modifiers components include ionizable polymers. The ionizable polymers of the present invention include linear, branched and/or crosslinked polymers. Of particular interest are carboxyvinyl polymers of monomers such as acrylic acid, methacrylic acid, ethacrylic acid, phenyl acrylic acid, pentenoic acid and the like. Poly(acrylic acid) and its salts is a preferred carboxyvinyl polymer. One or more poly(carboxyvinyl) polymers may be used in the polyoxyalkylene composition compositions of the present invention. Copolymers, such as by way of example only, copolymers of acrylic acid and methacrylic acid, are also contemplated.

Additional characteristics of the non-polyoxyalkylene component is its ability to provide mucosal adhesion. Bioadhesion or mucoadhesion is generally understood as the ability of a biological or synthetic material to "stick" to mucous membrane, resulting in adherence of the material to the tissue for protracted period of time. This concept has received a significant attention due to the potential applications in drug deliver and in enhanced drug bioavailability, which results from lengthening the period of time in which the bioadhesive dosage form is in contact with the targeted tissue versus standard dosage form. In order for the material to be bioadhesive, it must interact with mucus, which is highly hydrated, viscous anionic hydrogel layer protecting the mucosa. The mucin is composed largely of flexible glycoprotein chains, which are cross-linked. In order to obtain a bioadhesive system a few factors need to be analyzed carefully (Ahuja, A.; Khar, R. K; Ai, J. Mucoadhesive Drug Delivery Systems", *Drug Dev. Ind. Pharm.* 23(5):489 (1997)) First, the bioadhesive material has to be of high molecular weight polymers. These polymers entangled into the mucin layer forming a complex layer of polymers and mucin. Second, the presence of functional groups on the polymeric backbone is important as well. It was observed that hydrogen bonding plays an important roll in adhesion (Morrtazavi, S. A. "An in-vitro Assessment of Mucus Adhesive Interactions", *Intl. J. Pharm.,* 124(2):173 (1995)). Third, the surface energy, that is, the degree of hydrophobicity, plays an important role. When a good match is found between the polymers and the mucin, a good adhesion occurs (Lehr, C. M,; et. Al; "Oral Bioadhesive Drug Delivery Systems—Effects on GI Transit and Peptide Absorption", *Pharm. Res.,* 7(9), PDD 7226 (1990)). Finally, systems that swell in water will enhance the adhesion to the mucosa by dehydrating it and "pulling" the mucin chains into the delivery system.

Poly(acrylic acid) is a demonstrated bioadhesive polymer. It may be linear, branched and/or crosslinked. Poly(acrylic acid) is capable of ionization with a change in pH of the solution. By ionization, as that term is used with respect to poly(acrylic acid), it is meant the formation of the conjugate base of the acrylic acid, namely acrylate anion. As used herein, poly(acrylic acid) includes both ionized and non-ionized versions of the polymer. Changes in ionic strength may be accomplished by a change in pH or by a change in salt concentration. The viscosifying effect of the composition is partly a function of the ionization of the poly(acrylic acid); however, reverse thermal gelling may occur without ionization. Changes to the ionic state of the polymer causes the polymer to experience attractive (collapsing) or repulsive (expanding) forces. Where there is no need or desire for the composition to be applied in a high viscosity state, it may be possible to prepare the composition as non-ionized poly (acrylic acid). The body's natural buffering ability will adjust the pH of the applied composition to ionize the poly(acrylic acid) and thereby develop its characteristic viscosity.

Exemplary copolymers of the invention include:
$(CH_2CHR)_n$-Q-$(CH_2CH_2O)_x(CH_2CH(CH_3)O)_y$
$(CH_2CH_2O)_x$-Q-$(CH_2CHR)_m$, whereby a poloxamer is connected, at its termini, with a vinyl moiety. Q is a linking moiety and, in a preferred embodiment, Q is C—C, C—O, C(O)—NH, S—C, C(O)—O functionality and the like. R is a carboxyl, and n, m, x and y, are independently selected and in the range of 1 and 1000, or
$(CH_2CHR)_n$-Q-$(CH_2CH_2O)_x(CH_2CH(CH_3)O)_y$
$(CH_2CH_2O)_x$-Q-$(CH_2CHR)_n$-Q-$(CH_2CH_2O)_x(CH_2CH$
$(CH_3)O)_y(CH_2CH_2O)_n$-Q-$(CH_2CHR)_m$, in which alternating blocks of poloxamer and acrylic acid oligomers are joined. R and Q are as defined herein above. In preferred embodiments, a poloxamer is end-capped using acrylic acid oligomers with an ester linkage, or end-capped using acrylic acid oligomers with an ether linkage and R is COOH or $COOCH_3$.

Without intending to be bound by any particular mechanism or chemical structure, it is believed that the combination of biocompatible polymer component and the poloxamer component in a linear copolymer gives the composition its unique properties. Viscosity is a function of the molecular weight of the solubilized composition. Aggregation of the poloxamer component from a few molecules increases the effective molecular weight of the polymer network. The aggregation may be in the form of micelle formation, precipitation, labile crosslinking or other factors. The biocompatible polymer increases the molecular does not interfere with the poloxamer aggregation due to the linear block morphology of the polymer. The linear structure permits enhanced interaction of neighboring poloxamer units and maximizes access of the bioadhesive component to the site of administration.

The aggregation process may be understood as occurring as shown in FIG. 1, in which a polymer component 20 represents a biocompatible polymer, such as poly(acrylic acid), and region 24 represents the poloxamer component of the linear copolymer. The poloxamer includes a hydrophobic poly(propyleneoxide) region 26 and a hydrophilic poly (ethyleneoxide) region 28. Below the transition temperature, no aggregation os observed. At or above the transition temperature, the poloxamer regions 24 associate to form aggregations or micelles 30. The association increases the effective molecular weight of the composition with the corresponding increase in viscosity.

Figure 2:
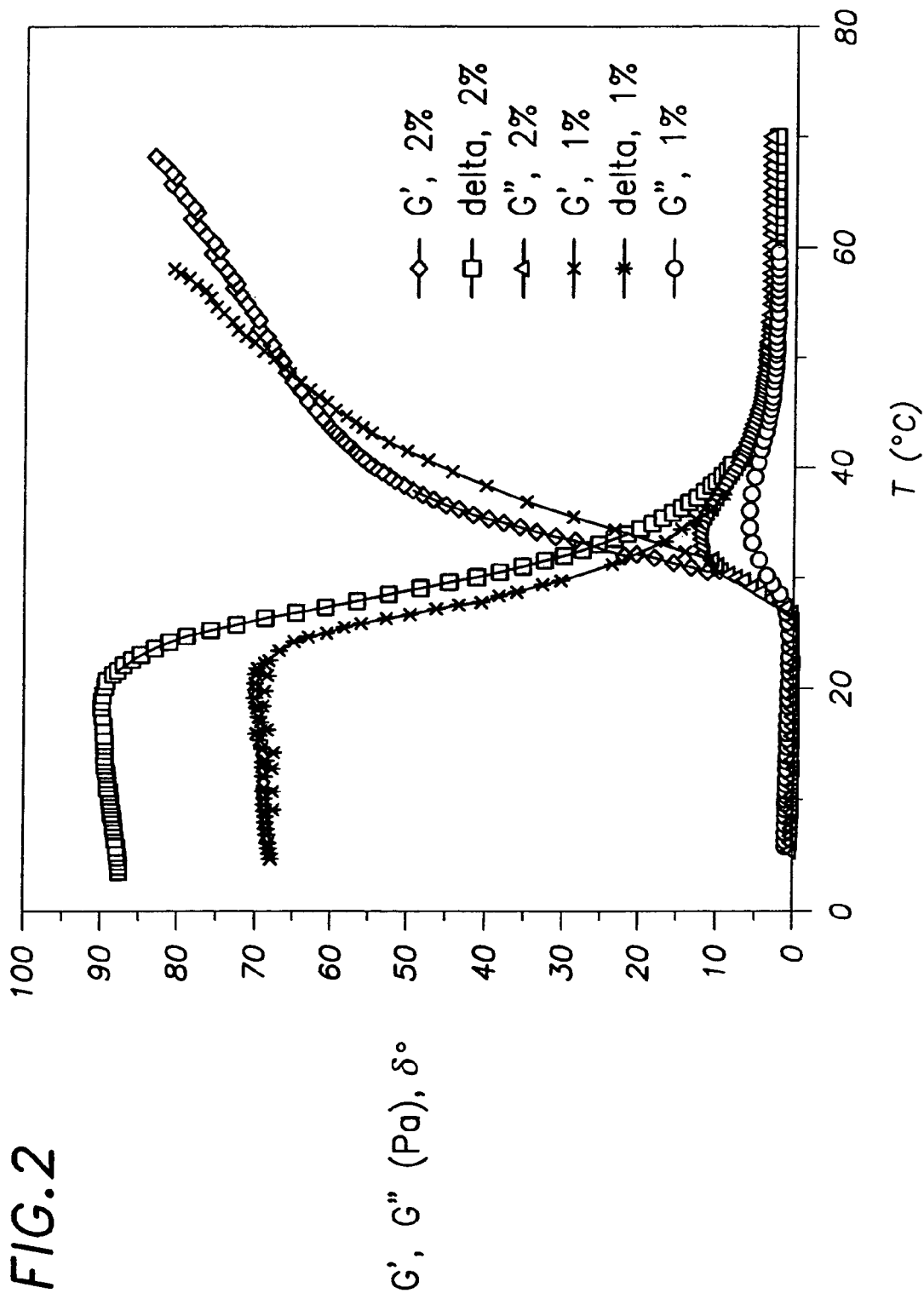
FIG. 2 is a graph of G', G" and δ° vs. temperature for a 1 wt % and 2 wt % of a poloxamer/poly(acrylic acid) (1:1) aqueous composition.

The temperature-sensitive viscosification of low solids content solutions (1 wt % and 2 wt %) of a PAA-end modified poloxamer copolymer prepared as described in Example 1 is shown in FIG. 2. Rheological properties (storage modulus, G', loss modulus, G", and loss angle $\delta°$) are reported over a temperature range of 5–70° C. The storage modulus is a measure of the mechanical strength of the system, which increases upon increased solution viscosity. The loss modulus measures the liquidity of the system, which decreases upon viscosification. Tan $\delta°$ is the relationship between the two, e.g., G"/G'. Even very dilute solutions exhibited a transition from Newtonian liquid at ambient temperature to a viscoelastic gel at body temperature.

Unlike many prior art hydrogels, e.g., carbomers, the poloxamer:poly(acrylic acid) composition does not permanently loose viscosity after being subjected to high shear conditions. The poloxamer:poly(acrylic acid) composition remains unaffected by such shear conditions as homogenization. No significant decrease in viscosity is observed.

A number of factors influence the viscosity and transition temperature of the composition. The more important factors include polymer concentration, pH and presence and nature of additives. Additives may be includes which shift the temperature of viscosification upwards or downwards. Suitable additives are those which disrupt or enhance the micelle forming capabilities of the poloxamer, respectively.

The linear copolymer may be prepared using conventional polymer synthetic methodology. For example, a poloxamer may be chemically reacted at the terminal hydroxyl groups to provide a polymerizable moiety. The moiety may be further reacted with monomers or oligomers of acrylic acid to provide the end-modified copolymer. A general method of making the end-modified poloxamer compositions of the present invention comprises solubilization of an end-activated poloxamer component in a monomer of the bioadhesive polymer, e.g., acrylic acid monomer, followed by polymerization of the monomer. Polymerization may be accomplished by addition of a polymerization initiator or by irradiation techniques. The initiator may be a free radical initiator, such as chemical free radical initiators and UV or gamma radiation initiators. Conventional free radical initiators may be used according to the invention, including, but in no way limited to ammonium persulfate, benzoin ethyl ether, benzyl peroxide, 1,2'-azobis(2,4-dimethylpentanitrile) (Vazo 52) and azobisisobutyronitrile (AIBN). Initiation may also be accomplished using cationic or anionic initiators. Many variations of this methods will be apparent to one skilled in the art and are contemplated as within the scope of the invention. For example, the poloxamer component may be dissolved in an acrylic acid/water mixture instead of pure monomer. It may be desirable to remove unreacted monomer and/or free poloxamer from the resultant polymer network. This may be accomplished using conventional techniques, such as, by way of example, dialysis or Sohxlet extraction. The interested reader is directed to L. Bromberg, "Polyether-modified poly(acrylic acid) synthesis and properties," *Ind. Eng. Chem. Res.*, 37(11): 4267–4274 (1998), for further details.

The reverse viscosification effect at low polymer concentrations provides clear, colorless gels which are particularly well-suited to pharmaceutic and personal care applications. For example, very little residue is formed upon dehydration which may be important in some applications, such as in optically applied pharmaceutics. An additional advantage of the composition of the invention is that it remains clear and translucent before and after the triggering environmental change. These characteristics of the reversibly gelling composition make it well suited for use in pharmaceutic compositions.

The practical advantage of this behavior of the composition is that the formulation can be administered as a flowing liquid at ambient temperatures. Upon contact with body tissues it viscosifies, thus changing its flow properties, and more importantly, its clearance from the site of application is dramatically reduced. Furthermore, for polymers in general, the viscosity at ambient temperature is concentration dependent. As the concentration is increased to achieve desired flow properties in contact with body tissues, the viscosity at ambient temperatures also increases, making it more difficult to administer such compositions.

Thus, a composition may be prepared at low temperatures while the composition is in a low viscosity state. Mixing of ingredients under low viscosity is expected to be easier, thus simplifying the manufacturing process. Yet, the resultant mixture would be of increased viscosity at use temperatures. As a further advantage, a composition comprising reversibly gelling composition may be spread thinly to allow for even application, due to its low viscosity at room temperature, but will thicken and "fill" the body contours upon warming up to body surface temperature.

The reversibly gelling composition may also be included in a composition for use as a stabilizing, solubilizing or emulsifying agent for a hydrophobic component of the formulation. Upon aggregation and/or micelle formation in the polyoxyalkylene component, hydrophobic domains are created which may be used to solubilize and control release of hydrophobic agents. Similar micelle-based systems have been shown to protect trapped peptides and proteins against enzymatic degradation from surface enzymes.

The reversible viscosification of the composition at elevated temperatures makes the materials ideal for use as thickening agents in pharmaceutic and personal care products at any temperature above the transition. Another use of the "thickening" of solutions containing the composition as a thickener supplement in emulsions. Currently emulsifiers are often negatively effected by increased temperatures. An additive with reverse thermal viscosification properties, however, would react in exactly the opposite way, increasing its ability to emulsify as it gained three-dimensional structure upon heating above its transition temperature.

In addition to the unique rheological properties provided by the reverse thermal composition, the reverse thermal composition is capable of solubilizing and releasing bioactive materials. Solubilization is expected to occur as a result of dissolution in the bulk aqueous phase or by incorporation of the solute in micelles created by the hydrophobic domains of the poloxamer. Release of the drug would occur through diffusion or network erosion mechanisms.

In the applications where the reversibly gelling polymer composition can act as a surfactant, the composition will have the ability to act as a primary emulsifier without any (or with very little) addition of traditional surfactant. The polyoxyalkylene composition will also act as a stabilizer for oil-soluble ingredients that would conventionally need to be solubilized by oils in formulation. The hydrophobic portion of the composition (PPO) forms domains which act as reservoirs for an oil-soluble or hydrophobic additive, such as a hydrophobic pharmaceutical agent. The increase in viscosity above the transition temperature adds structure and yield value to the water phase and results in a highly stable emulsion for the hydrophobic additive.

The composition may be useful as a solubilization agent in pharmaceutic and personal care applications. A self-assembling system comprising the reversibly gelling composition exhibits thermogelation, pH sensitivity, and the ability to solubilize hydrophobic agents in aqueous media. When poloxamer is copolymerized with poly(acrylic acid) (PAA) according to the invention, the resulting composition is bioadhesive and can be applied in a number of therapies. The materials described in this invention combine "reverse" thermoviscosification mucoadhesion, solubilization of hydrophobic and difficult to manage moieties, easy formulation, and protection of agents from degradation to provide a superior medium for pharmaceutic and personal care products.

Those skilled in the art will appreciate that the composition compositions of the present invention may be utilized for a wide variety of pharmaceutic and personal care applications. To prepare a pharmaceutic composition, an effective amount of pharmaceutically active agent(s) which imparts the desirable pharmaceutic effect is incorporated into the reversibly gelling composition of the present invention. Preferably the selected agent is water soluble, which will readily lend itself to a homogeneous dispersion through out the reversibly gelling composition; however, the composition has been demonstrated to significantly solubilize or suspend hydrophilic agents in order to improve formulation homogeneity. It is also preferred that the agent(s) is nonreactive with the composition. For materials which are not water soluble, it is also within the scope of the invention to disperse or suspend lipophilic material throughout the composition.

A discussion of particular applications and formulations follows.

Esophageal, oral cavity and buccal applications. One indication for the use of this reverse thermal composition would be as a coating to protect tissue from external or internal chemical challenges. For example, the hydrogel in the form of an esophageal formulation could coat the esophagus and protect it from the effects of acid, resulting from gastric reflux (GERD). Because of its ionic nature, the neutralized, polyacrylic acid component of the reverse thermal composition could neutralize a certain amount of acid and prevent the acid from acting upon the tissue. In another variation, the reverse thermal composition formulation could include acid absorbing substances, such as, aluminum oxide.

With the incorporation of bioactive materials, the hydrogel provides a suitable vehicle for delivering drugs within the esophageal lining. As explained above, its rheological and mucoadhesive properties are desirable attributes for controlling and facilitating drug delivery. The shear sensitivity of the polymer could also be taken advantage of in applications in which a liquid treatments is sprayed under high shear conditions onto the oral cavity, where the solution adheres and viscosifies to provide a reservoir for antibacterial agents, such as chlorohexadine, or a breath freshener.

Ophthalmic applications. Most ophthalmic drugs are applied to the eye topically to the precorneal area. The most common dosage form is a liquid drop. Drug bioavailability is generally low because liquid formulations are quickly cleared from the eye by tearing and blinking, resulting in the need for frequent dosing and uneven drug delivery.

The end-modified hydrogel composition provides a new vehicle for achieving greater bioavailability of topically administered ophthalmic drugs. Formulations containing it can be applied as drops which viscosity or gel upon contact with eye. Since gelling can be accomplished with low concentrations of the polymer, blurring can be minimized upon drop instillation. Low solid concentrations also help to minimize crusting along the eyelid margins.

A particular advantage of the hydrogel is that, as a result of its Theological properties, compositions containing the polymer will evenly coat the precorneal surface. This is in contrast to other ophthalmic drug delivery vehicles which may gel upon application to the eye but which form deposits of the formulation that reside under one eyelid. The ability of the polymer to shear-thinning or to evenly spread over the precorneal surface is particularly advantageous in dry eye formulations or in the treatment of inflammation and wound healing conditions.

The use of the end-modified hydrogel composition would be indicated for delivering bioactive materials, such as, anesthetics, mydriatics and cycloplegics, antimicrobial agents (antibacterial, antifungal, antiviral), anti-inflammatory agents, agents for the treatment of glaucoma, ocular decongestants, diagnostic agents, and wound healing agents.

Nasal applications. The use of the end-modified hydrogel composition is also indicated for the delivery of drugs to the nasal cavity. Nasal drug delivery has been considered as an alternative to parenteral routes of administration of drugs that demonstrate low oral bioavailability. In order to increase the bioavailability of nasally administered drugs, efforts have been made to increase the residence time of formulations in the nasal cavity. Nasal delivery of drugs can offer advantages over other methods of delivery, including rapid systemic absorption, lower dosing, more rapid onset of desired therapeutic effects, and improved pharmacokinetics. In addition, it provides an alternative route for administering peptide drugs, which generally have low bioavailability via the oral route and are normally administered parenterally.

The rheological properties of the reverse thermal composition are uniquely suited to nasal delivery systems. Earlier results demonstrated that formulation variables can be manipulated to significantly affect the higher temperature viscosity of the reverse thermal composition. These same variables have only minimal effects on the low temperature viscosity. Therefore, formulations containing the end-modified hydrogel composition can be readily sprayed at low temperature; the subsequent viscosification occurs only after administration of the formulation and only at the site of application.

The end-modified hydrogel composition is also useful for delivering agents such as decongestants, antihistamines, anti-osteoporosis agents, hormones, antineoplastic agents, Parkinsonism drugs, etc. The composition is also indicated for the application of vaccines, such as those against the influenza virus.

A further desirable outcome of the use of the end-modified hydrogel composition in the delivery of nasal formulations is the prevention of roll back, or the loss of the formulation by rapid flow to the posterior section of the nasal cavity and into the esophagus. In addition to the negative effects on the delivery of the drug across the desired mucosal tissue, roll can lead to unpleasant taste sensations associated with some drug formulations.

Another desirable outcome of the use of the end-modified hydrogel composition in the delivery of nasal formulations is the prevention of drip, or the loss of the formulation by flow outward due to gravity. In addition to the negative effects on the delivery of the drug across the desired mucosal tissue, drip leads to undesirable consumer appeal and therefore reduces the use of such drug formulations.

Vaginal/rectal applications. The use of the end-modified hydrogel composition is also indicated for the delivery of drugs to the vaginal or the rectal cavity. These drug delivery routes have been considered as an alternative to parenteral routes of administration of drugs that demonstrate low oral bioavailability. In order to increase the bioavailability of vaginally or rectally administered drugs, efforts have been made to increase the residence time of formulations in those cavities. These routes offer advantages over other methods of delivery, including rapid systemic absorption, lower dosing, more rapid onset of desired therapeutic effects, and improved pharmacokinetics.

The rheological properties of the reverse thermal composition are uniquely suited to both vaginal and rectal delivery systems. Such formulations containing the end-modified hydrogel composition can be readily applied at low temperature in a liquid or semi-liquid form to allow consumer preferred format for administration; the subsequent viscosification occurs only after administration of the formulation and only at the site of application to eliminate the leak-back that is typical undesired effect of current formulations.

Veterinary applications. The reversibly gelling composition of the invention also may be useful in the treatment of not only human conditions but in providing treatments for animal care. For veterinary products, the end-modified hydrogel composition is indicated for the preparation of topical dermal products, such as antibacterials, antifungals, antipruritics, and antiseborrheia, antiodor, and antiseptic/wound healing preparations. Otic products would include ear cleaners with or without actives, such as, antifungals. Ophthalmic products would include eye moisturizers or antimicrobial preparations. The rheological, solubilizing, drug delivery, and chemical properties provide the formulator of veterinary products the latitude to prepare compositions in a variety of delivery forms and, more importantly, with regard to companion animals, with a non-oily quality.

Tablet Excipients. It has been demonstrated that standard pharmaceutical processes, such as lyophilization and air-drying can process the hydrogel of the invention. The reversible thermal viscosifying hydrogel may be reconstituted with water, phosphate buffer or calcium chloride solution, without loss or degradation of the rheological properties of the polymer. Thus, it is contemplated that the hydrogel of the invention may also be incorporated as excipients into tablets or granules for oral delivery. The polymer may be coated on an outer surface of the tablet or may be introduced in powder form into the tablet along with the active agent and other ingredients. The poloxamer:poly (acrylic acid) composition may be used to promote bioadhesion of the tablet and its contents with the mucosal lining of the gastro-intestinal tract to extend transit time.

Also, when incorporated as a powder, the slow dissolution rate of the end-modified hydrogel makes it a suitable excipient to sustained release tableting formulation. The addition of such hydrogel would yield to a slow release of the incorporated drug.

Injectibles. The end-modified hydrogel composition of the invention is well-suited for use in injectable applications. A depot formulation may be prepared and administered at low viscosity to a subdermal or intramuscular site, for example. The polymer will viscosify and form a depot site, which will slowly release the active agent. The reversible thermally viscosifying polymer network, upon contact with body fluids including blood or the like, undergoes gradual release of the dispersed drug for a sustained or extended period (as compared to the release from an isotonic saline solution). This can result in prolonged delivery (over, say 1 to 2,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Alternatively, the end-modified hydrogel composition may be prepared at higher viscosifies in order to suspend microspheres or particles in the formulation. The formulation can then take advantage of the shear thinning properties of the polymeric material. Thus, during injection, the formulation is subjected to shear stresses which reduce viscosity and allow an ordinarily viscous formulation to be introduced into the patient by injection. Cessation of the strain results in reestablishing the high viscosity of the formulation, so that the active agent may be slowly released therefrom.

The end-modified hydrogel composition is effective in extending the duration of contact of preparations that have been applied to mucosal tissues. In providing a longer residence time, the reverse thermal composition provides a valuable tool for increasing drug delivery across mucosal surfaces.

The end-modified hydrogel composition also may be used for products in which there is no bioactive ingredient. The function of the composition would be to provide, for example, a protective or lubricating film to the surface of the tissue. For example, the composition could be the basic ingredient for a lubricating drop for the eye. By its nature, that is, that of a hydrogel, it could provide a long lasting lubricious and moisturizing film to the eye of individuals suffering from dry eye conditions due to pathological states or environmental stress. Other similar indications would be for nasal or vaginal moisturizers.

It will also be appreciated that a sterile environment may be required. It is contemplated as within the scope of the invention that the reversibly gelling composition compositions of the present invention may be prepared under sterile conditions.

In the preparation of pharmaceutical compositions, problems can be encountered in the solubilization of hydrophobic bioactive materials. Because of its hydrophobic moieties, the end-modified hydrogel composition is capable of facilitation such dissolution, even at the low concentrations which are used in formulating.

Preparation of pharmaceutic compositions may be accomplished with reference to any of the pharmaceutic formulation guidebooks and industry journals which are available in the pharmaceutic industry. These references supply standard formulations which may be modified by the addition or substitution of the reversible viscosifying composition of the present invention into the formulation. Suitable guidebooks include *Pharmaceutics and Toiletries Magazine*, Vol. 111 (March, 1996); *Formulary: Ideas for Personal Care*; Croda, Inc, Parsippany, N.J. (1993); and *Pharmaceuticon: Pharmaceutic Formulary*, BASF, which are hereby incorporated in their entirety by reference.

The pharmaceutic composition may be in any form. Suitable forms will be dependant, in part, of the intended mode and location of application. Ophthalmic and otic formulations are preferably administered in droplet or liquid form; nasal formulations are preferable administered in droplet or spray form, or may be administered as a powder (as a snuff); vaginal and rectal formulations are preferably administered in the form of a cream, jelly or thick liquid; veterinary formulations may be administered as a cream, lotion, spray or mousse (for application to fur or exterior surface); esophageal and buccal/oral cavity applications are preferably administered from solution or as a powder; film forming applications or dermal applications may be administered as a lotions, creams, sticks, roll-ons formulations or pad-applied formulations.

Exemplary drugs or therapeutics delivery systems which may be administered using the aqueous responsive composition compositions of the invention include, but are in no way limited to, mucosal therapies, such as esophageal, otic, rectal, buccal, oral, vaginal, and urological applications; topical therapies, such as wound care, skin care and teat dips; and intravenous/subcutaneous therapies, such as intramuscular, intrabone (e.g., joints), spinal and subcutaneous therapies, tissue supplementation, adhesion prevention and parenteral drug delivery. In addition, further applications include transdermal delivery and the formation of depots of drug following injection. It will be appreciated that the ionic nature of the biocompatible component of the responsive composition provides an adhesive interaction with mucosal tissue.

Because the reversibly gelling composition of the present invention is suited for application under a variety of physiological conditions, a wide variety of pharmaceutically active agents may be incorporated into and administered from the composition. The pharmaceutic agent that may be loaded into the polymer networks of the present invention are any substance having biological activity, including proteins, polypeptides, polynucleotides, nucleoproteins, polysaccharides, glycoproteins, lipoproteins, and synthetic and biologically engineered analogs thereof.

Examples of suitable pharmaceutic agents that might be utilized in a delivery application of the invention include literally any hydrophilic or hydrophobic biologically active compound. Preferably, though not necessarily, the drug is one that has already been deemed safe and effective for use by the appropriate governmental agency or body. For example, drugs for human use listed by the FDA under 21 C.F.R. 330.5, 331 through 361; 440–460; drugs for veterinary use listed by the FDA under 21 C.F.R. 500–582. incorporated herein by reference, are all considered acceptable for use in the present novel polymer networks.

The compositions of the invention include a safe and effective amount of a pharmaceutically active agent. "Safe and effective", as it is used herein, means an amount high enough to significantly positively modify the condition to be treated or the pharmaceutic effect to be obtained, but low enough to avoid serious side effects. As is mentioned herein above, compositions of the invention are considered to include both pharmaceutical agents which treat the source or symptom of a disease or physical disorder and personal care or cosmetic agents which promote bodily attractiveness or mask the physical manifestations of a disorder or disease.

Drugs that are not themselves liquid at body temperature can be incorporated into polymers, particularly gels. Moreover, peptides and proteins which may normally be lysed by tissue-activated enzymes such as peptidases, can be passively protected in gels as well. See, Gehrke et al. *Proceed. Intern. Symp. Control. Rel.* Bioact. Mater., 22:145 (1995).

The variety of different therapeutic agents which can be used in conjunction with the copolymers of the invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins. Suitable pharmaceuticals for parenteral administration are well known as is exemplified by the Handbook on Injectable Drugs, 6th edition, by Lawrence A. Trissel, American Society of Hospital Pharmacists, Bethesda, Md., 1990 (hereby incorporated by reference).

Pharmaceutic agents includes pharmacologically active substances that produce a local or systemic effect in animals, plants, or viruses. The term thus means any substance intended for use in the diagnosis, cure, mitigation, treatment or prevention of disease or in the enhancement of desirable physical or mental development and conditions in an animal, plant, or virus. The term "animal" used herein is taken to mean mammals, such as primates, including humans, sheep, horses, cattle, pigs, dogs, cats, rats, mice; birds; reptiles; fish; insects; arachnids; protists (e.g. protozoa); and prokaryotic bacteria. The term "plant" means higher plants (angiosperms, gymnosperms), fungi, and prokaryotic blue-green "algae" (i.e. cyanobacteria).

The pharmaceutically active compound may be any substance having biological activity, including proteins, polypeptides, polynucleotides, nucleoproteins, polysaccharides, glycoproteins, lipoproteins, and synthetic and biologically engineered analogs thereof. The term "protein" is art-recognized and for purposes of this invention also encompasses peptides. The proteins or peptides may be any biologically active protein or peptide, naturally occurring or synthetic.

Examples of proteins include antibodies, enzymes, steroids, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules. The pharmaceutical agents may be selected from insulin, antigens selected from the group consisting of MMR (mumps, measles and rubella) vaccine, typhoid vaccine, hepatitis A vaccine, hepatitis B vaccine, herpes simplex virus, bacterial toxoids, cholera toxin B-subunit, influenza vaccine virus, bordetela pertussis virus, vaccinia virus, adenovirus, canary pox, polio vaccine virus, plasmodium falciparum, bacillus calmette geurin (BCG), klebsiella pneumoniae, HIV envelop glycoproteins and cytokins and other agents selected from the group consisting of bovine somatropine (sometimes referred to as BST), estrogens, androgens, insulin growth factors (sometimes referred to as IGF), interleukin I, interleukin II and cytokins. Three such cytokins are interferon-$\beta$, interferon-$\gamma$ and tuftsin.

Examples of bacterial toxoids are tetanus, diphtheria, pseudomonas A, mycobacterium tuberculosis. Examples of HIV envelop glycoproteins are gp 120 and gp 160 for AIDS vaccines. Examples of anti-ulcer $H_2$ receptor antagonists are ranitidine, cimetidine and famotidine, and other anti-ulcer drugs are omparazide, cesupride and misoprostol. An example of a hypoglycaemic agent is glizipide. Insulin is used for the control of diabetes.

Classes of pharmaceutically active compounds which can be loaded into the indmodified hydrogel include, but are not limited to, anti-AIDS substances, anti-cancer substances, antibiotics, immunosuppressants (e.g. cyclosporine) antiviral substances, enzyme inhibitors, neurotoxins, opioids, hypnotics, antihistamines, lubricants tranquilizers, anti-convulsants, muscle relaxants and anti-Parkinson substances, anti-spasmodics and muscle contractants, miotics and anti-cholinergics, anti-glaucoma compounds, anti-parasite and/or anti-protozoal compounds, anti-hypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, and vaccines.

A more complete listing of classes of compounds suitable for loading into polymers using the present methods may be found in the *Pharmazeutische Wirkstoffe* (Von Kleemann et al. (Eds) Stuttgart/New York, 1987, incorporated herein by reference). A more complete list of suitable pharmaceutic agents can be found in WO 97/00275, which is hereby incorporated by reference.

Exemplary pharmaceutical agents considered to be particularly suitable for incorporation into the pharmaceutical composition of the invention with retention of therapeutic effectiveness and other advantageous properties include but are not limited to imidizoles, such as miconazole, econazole, terconazole, saperconazole, itraconazole, metronidazole, fluconazole, ketoconazole, and clotrimazole, luteinizing-hormone-releasing hormone (LHRH) and its analogues, nonoxynol-9, a GnRH agonist or antagonist, natural or synthetic progestrin , such as selected progesterone, 17-hydroxyprogeterone derivatives such as medroxyprogesterone acetate, and 19-nortestosterone analogues such as norethindrone, natural or synthetic estrogens, conjugated estrogens, estradiol, estropipate, and ethinyl estradiol, bisphosphonates including etidronate, alendronate, tiludronate, resedronate, clodronate, and pamidronate, calcitonin, parathyroid hormones, carbonic anhydrase inhibitor such as felbamate and dorzolamide, a mast cell stabilizer such as xesterbergsterol-A, lodoxamine, and cromolyn, a prostaglandin inhibitor such as diclofenac and ketorolac, a steroid such as prednisolone, dexamethasone, fluromethylone, rimexolone, and lotepednol, an antihistamine such as antazoline, pheniramine, and histiminase, pilocarpine nitrate, a beta-blocker such as levobunolol and timolol maleate, a sunscreen agent, an acne medication such as salicylic acid, sulfur, resorcinol, resorcinol monoacetate, and benzoyl peroxide, an anti-dandruff medication such as coal tar, pyrithione zinc, salicylic acid, selenium sulfide, and sulfur, a dermatological agent such as bath oils, emollients, hydrating agents, astringents, antipruritics, protectants, keratin-softening agents, and hydrocortisone, hydroquinone, or nicotine.

As will be understood by those skilled in the art, two or more pharmaceutical agents may be combined for specific effects. The necessary amounts of active ingredient can be determined by simple experimentation.

This material meets many of the requirements for an optimum transmucosal delivery system for proteins, including peptides. Effective and efficient delivery involves four primary elements: a method of holding an optimal quantity of peptides against the mucosa for an extended period; a method of controlling the release of the peptides in a desired pattern (e.g., burst, sustained, circadian, etc.), transferring the peptides from the mucosal surface to the blood sera or other target, and maintenance of activity of peptides. The measure of merit is the reliable achievement of a desired pharmaceutical effect with minimal wasted active material-for example, the achievement and sustaining of an effective level of active peptide in the blood stream for a given time period with minimal excess delivery and minimal loss of activity through inactivation or erosion.

The composition of the invention can be chosen for protein delivery. The biocompatible polymer component can be a mucoadhesive material (acrylic acid). The component can be a material which erodes (acrylic acid) or one that degrades (hyaluronic acid). The backbone can be crosslinked, can involve co-monomers, and can be of varying molecular weights or structures. These modifications to the backbone directly effect retention of the Peptide-gel system, patterns of release, and peptide activity.

In addition to the poloxamer:poly(acrylic acid) hydrogel, additional pharmaceutically acceptable carriers may be included in the composition, such as by way of example only, emollients, surfactants, humectants, powders and other solvents.

Preservatives can be desirably incorporated into the pharmaceutic compositions of the invention to protect against the growth of potentially harmful microorganisms. Suitable preservatives include, but are not limited to, alkyl esters of para-hydroxybenzoic acid, hydantoin derivatives, parabens, propioniate salts, triclosan tricarbanilide, tea tree oil, alcohols, farnesol, farnesol acetate, hexachlorophene and quaternary ammonium salts, such as benzolconjure, and a variety of zinc and aluminum salts. Pharmaceutic chemists are familiar with appropriate preservatives and may selects that which provides the required product stability. Preservatives are preferably employed in amounts ranging from about 0.0001% to 2% by weight of the composition.

Emollients can be desirably incorporated into the pharmaceutic compositions of the invention to provide lubricity to the formulation. Suitable emollients may be in the form of volatile and nonvolatile silicone oil, highly branched hydrocarbons and synthetic esters. Amounts of emollients may be in the range of about 0. 1–30 wt %, and preferably about 1–20 wt %. A variety of oily emollients may be employed in the compositions of this invention. These emollients may be selected from one or more of the following classes: triglyceride esters; acetoglyceride esters; ethoxylated glycerides; alkyl esters of fatty acids having 10 to 20 carbon atoms; alkenyl esters of fatty acids having 10 to 20 carbon atoms; fatty acids having 10 to 20 carbon atoms; fatty alcohols having 10 to 20 carbon atoms; fatty alcohol ethers, such as ethoxylated fatty alcohols of 10 to 20 carbon atoms having attached thereto from 1 to 50 ethylene oxide groups or 1 to 50 propylene oxide groups; ether-esters such as fatty acid esters of ethoxylated fatty alcohols; lanolin and derivatives; polyhydric alcohol esters; wax esters; beeswax derivatives; vegetable waxes including carnauba and candelilla waxes; phospholipids; sterol including cholesterol and cholesterol fatty acid esters; and amides such as fatty acid amides, ethoxylated fatty acid amides, solid fatty acid alkanolamides.

Humectants may be added to the composition to increase the effectiveness of the emollient, to reduce scaling, to stimulate removal of built-up scale and improve skin feel. The amount of humectant may be in the range of about 0.5–30 wt % and preferably between 1–15 wt %.

By way of example only, in the case of antibiotics and antimicrobials may be included in the composition of the invention. Antimicrobial drugs preferred for inclusion in compositions of the present invention include salts of lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole and amanfadine and the like.

Personal Care Applications: The reverse viscosification effect at low polymer concentrations provides clear, colorless gels that are particularly well suited for cosmetic applications. For example, very little residue is formed upon dehydration which may be important in some applications, such as in topically applied cosmetics. An additional advantage of the composition of the invention is that it remains clear and translucent above and below the critical temperature or pH. These characteristics of the reversibly gelling composition make it well suited for use in cosmetic compositions.

The composition of the present invention technology may be added to cosmetic formulations to increase the thickness and viscosity of the composition. The poloxamer:poly (acrylic acid) possesses hydrophobic regions capable of aggregation. Unlike conventional thickeners, the aggregation of the composition of the present invention is temperature sensitive. Thus, the inventive composition of the present invention may have a transition temperature (i.e. temperature of aggregation) above room temperature so that the cosmetic composition is of low viscosity at or below room temperature and is of high viscosity at or around body temperature (body temperature includes both surface and internal body temperature). Thus, a composition may be prepared at low temperatures while the composition is in a low viscosity state. Mixing of ingredients under low viscosity is expected to be easier, thus simplifying the manufacturing process. Yet, the resultant mixture would be of increased viscosity at use temperatures. As a further advantage, a cosmetic composition comprising poloxamer:poly (acrylic acid) may be spread thinly to allow for even application, due to its low viscosity at room temperature, but will thicken and "fill" the skin contours upon warming up to body surface temperature.

In another aspect of the invention, the composition may be applied through a nozzle that provides high shear to reduce viscosity, yet the composition regains its viscosity after application to the skin. This contrasts with conventional formulations which permanently lose viscosity after being subjected to high shear.

In another aspect of the invention, the composition may be formulated and applied as a liquid, spray, semi-solid gel, cream, ointment, lotion, stick, roll-on formulation, mousse, pad-applied formulation, and film-forming formulation.

The poloxamer:poly(acrylic acid) composition may also be included in a personal care or cosmetic composition for use as a stabilizing, solubilizing or emulsifying agent for a hydrophobic component of the cosmetic formulation. The strong hydrophilic regions of the poloxamer resulting from aggregation and micelle formation create hydrophobic domains which may be used to solubilize and control release of hydrophobic agents. Similar micelle-based systems have been shown to protect trapped peptides against enzymatic degradation from surface enzymes.

Those skilled in the art will appreciate that the composition compositions of the present invention may be utilized for a wide variety of cosmetic and personal care applications. To prepare a cosmetic composition, an effective amount of cosmetically active agent(s) that imparts the desirable cosmetic effect is incorporated into the reversibly gelling composition of the present invention. Preferably the selected agent is water soluble, which will readily lend itself to a homogeneous dispersion through out the reversibly gelling composition; however, the composition has been demonstrated to significantly solubilize or suspend hydrophilic agents in order to improve formulation homogeneity. It is also preferred that the agent(s) is nonreactive with the composition. For materials which are not water soluble, it is also within the scope of the invention to disperse or suspend powders or oil (lipophilic materials) throughout the composition. It will also be appreciated that some applications may require a sterile environment. It is contemplated as within the scope of the invention that the reversibly gelling composition compositions of the present invention may be prepared under sterile conditions. An additional feature of the reversibly gelling polymer composition is that is prepared from constituent polymers that have known accepted toxicological profiles.

Exemplary cosmetic and personal care applications, for which the reversibly gelling composition may be used include, but are not limited to, baby products, such as baby shampoos, lotions, powders and creams; bath preparations, such as bath oils, tablet and salts, bubble baths, bath fragrances and bath capsules; eye makeup preparations, such as eyebrow pencil, eyeliner, eye shadow, eye lotion, eye makeup remover and mascara; fragrance preparations, such as colognes and toilet waters, powders and sachets; noncoloring hair preparations, such as hair conditioner, hair spray, hair straighteners, permanent waves, rinses shampoos, tonics, dressings and other grooming aids; color cosmetics; hair coloring preparations such as hair dye, hair tints, hair shampoos, hair color sprays, hair lighteners and hair bleaches; makeup preparations such as face powders, foundations, leg and body paints, lipstick, makeup bases, rouges and makeup fixatives; manicuring preparations such as basecoats and undercoats, cuticle softeners, nail creams and lotions, nail extenders, nail polish and enamel, and nail polish and enamel remover; oral hygiene products such as dentrifices and mouthwashes; personal cleanliness, such as bath soaps and detergents, deodorants, douches and feminine hygiene product; shaving preparations such as aftershave lotion, beard softeners, men's talcum, shaving cream, shaving soap and preshave lotions; skin care preparations such as cleansing preparations, skin antiseptics, depilatories, face and neck cleansers, body and hand cleansers, foot powders and sprays, moisturizers, night preparations, paste masks, and skin fresheners; and suntan preparations such as suntan creams, gels and lotions, indoor tanning preparations.

Preparation of the above-named cosmetic compositions and others may be accomplished with reference to any of the cosmetic formulation guidebooks and industry journals which are available in the cosmetic industry. These references supply standard formulations which may be modified by the addition or substitution of the reversible viscosifying composition of the present invention into the formulation. Suitable guidebooks include *Cosmetics and Toiletries Magazine*, Vol. 111 (March, 1996); *Formulary: Ideas for Personal Care*; Croda, Inc, Parsippany, N.J. (1993); and *Cosmeticon: Cosmetic Formulary*, BASF, which are hereby incorporated in their entirety by reference.

The cosmetic composition may be in any form. Suitable forms include but are not limited to lotions, creams, sticks, roll-ons formulations, mousses, aerosol sprays, pad-applied formulations, and film-forming formulations.

As those skilled in the art will appreciate, the foregoing list is exemplary only. Because the reversibly gelling composition of the present invention is suited for application under a variety of physiological conditions, a wide variety of cosmetically active agents may be incorporated into and administered from the composition. In addition to the poloxamer:poly(acrylic acid) polymer network, additional cosmetically acceptable carriers may be included in the composition, such as by way of example only, emollients, surfactants, humectants, powders and other solvents. By way of example only, the cosmetic composition also may include additional components, which serve to provide additional aspects of the cosmetic affect or to improve the stability and/or administration of the cosmetic. Such additional components include, but are not limited to, preservatives, abrasives, acidulents, antiacne agents, anti-aging agents, antibacterials, anticaking, anticaries agents, anticellulites, antidandruff, antifungal, anti-inflammatories, anti-irritants, antimicrobials, antioxidants, astringents. anitperspirants, antiseptics, antistatic agents, astringents, binders, buffers, additional carriers, chelators, cell stimulants, cleansing agents, conditioners, deodorants, dipilatories, detergents, dispersants, emollients, emulsifiers, enzymes, essential oils, exfoliants, fibers, film forming agents, fixatives, foaming agents, foam stabilizers, foam boosters, fungicides, gellants, glosser, hair conditioner, hair set resins, hair sheen agents, hair waving agents, humectants, lubricants, moisture barrier agents, moisturizers, ointment bases, opacifier, plasticizer, polish, polymers, powders, propellant, protein, refatting agents, sequestrant, silicones, skin calming agents, skin cleansers, skin conditioners, skin healing, skin lightening agents, skin protectants, skin smoothing agents, skin softening agents, skin soothing agents, stabilizers, sunscreen agents, surfactants, suspending agents, tanning accelerators, thickeners, vitamins, waxes, wetting agents, liquefiers, colors, flavors and/or fragrances . Suitable materials which serve the additive functions listed here are well known in the cosmetic industry. A listing of the additive function and materials suitable for incorporation into the cosmetic composition may be found in Appendix A, which is appended hereto at the end of the specification. Further information may be obtained by reference to *The Cosmetic Bench Handbook*, Cosmetics & Toiletries; C. C. Urbano, editor, Allured Publ. Corp., 1996. which is hereby incorporated in its entirety by reference.

A brief description of some preferred additives and cosmetically active agents follows. The compositions of the invention include a safe and effective amount of a cosmetically active agent. "Safe and effective", as it is used herein, means an amount high enough to significantly positively modify the condition to be treated or the cosmetic effect to be obtained, but low enough to avoid serious side effects.

Preservatives and emollients can be desirably incorporated into the cosmetic compositions of the invention, such as those described above for pharmaceutical compositions. A variety of oily emollients may be employed in the compositions of this invention. These emollients may be selected from one or more of the following classes: 1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalene, Kikui oil and soybean oil. 2. Acetoglyceride esters, such as acetylated monoglycerides; 3. Ethoxylated glycerides, such as ethoxylated glyceryl monostearate; 4. Alkyl esters of fatty acids having 10 to 20 carbon atoms, such as, methyl, isopropyl, and butyl esters of fatty acids, and including hexyl laurate, isohexyl laurate, isohexyl palmitate, isopropyl palmitate, decyl oleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; 5. alkenyl esters of fatty acids having 10 to 20 carbon atoms, such as oleyl myristate, oleyl stearate, and oleyl oleate and the like; 6. fatty acids having 10 to 20 carbon atoms, such as pelargonic, lauric, myristic, palmitic, stearic, isostearic, hydroxystearic, oleic, linoleic, ricinoleic, arachidic, behenic, and erucic acids and the like; 7. fatty alcohols having 10 to 20 carbon atoms, such as, lauryl, myristyl, cetyl, hexadecyl, stearyl, isostearyl, hydroxystearyl, oleyl, ricinoleyl, behenyl, erucyl, and 2-octyl dodecanyl alcohols are examples of satisfactory fatty alcohols and the like, 8. fatty alcohol ethers, such as ethoxylated fatty alcohols of 10 to 20 carbon atoms including the lauryl, cetyl, stearyl, isostearyl, oleyl, and cholesterol alcohols, having attached thereto from 1 to 50 ethylene oxide groups or 1 to 50 propylene oxide groups; 9. ether-esters such as fatty acid esters of ethoxylated fatty alcohols; 10. Lanolin and derivatives, such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases and the like; 11. polyhydric alcohol esters, such as, ethyleneoxide mono and di-fatty acid esters, diethyleneoxide mono-and di-fatty acid esters, polyethyleneoxide (200–6000) mono- and di-fatty acid esters, propyleneoxide mono- and di-fatty acid esters, polypropyleneoxide 2000 monooleate, polypropyleneoxide 2000 monostearate, ethoxylated propyleneoxide monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters; 12. wax esters such as beeswax, spermaceti, myristyl myristate, stearyl stearate; 13. beeswax derivatives, e.g. polyoxyethylene sorbitol beeswax; 14. vegetable waxes including carnauba and candelilla waxes; 15. phospholipids such as lecithin and derivatives; 16. sterol including cholesterol and cholesterol fatty acid esters; 17. amides such as fatty acid amides, ethoxylated fatty acid amides, solid fatty acid alkanolamides.

Humectants may be added to the composition to increase the effectiveness of the emollient, to reduce scaling, to stimulate removal of built-up scale and improve skin feet. By way of example only, suitable humectants include polyhydric alcohols, such as glycerol, polyalkylene glycols, alkylene polyols their derivatives, propyleneoxide, dipropyleneoxide, polypropyleneoxide, polyethyleneoxide, sorbitol, hydroxypropyl sorbitol, hexylene glycol, 1,3-butylene glycol, 1,2,6-hexanetriol, ethoxylated glycerol, propoxylated glycerol and the like. The amount of humectant may be in the range of about 0.5–30 wt % and preferably between 1–15 wt %.

In topical skin care applications, a variety of active substances may be advantageously employed. By way of example only suitable active agents which may be incorporated into the cosmetic composition include anti-aging active substances, anti-wrinkle active substances, hydrating or moisturizing or slimming active substances, depigmenting active substances, substances active against free radicals, anti-irritation active substances, sun protective active substances, anti-acne active substances, firming-up active substances, exfoliating active substances, emollient active substances, and active substances for the treating of skin disorders such as dermatitis and the like.

By way of example only, in the case of hydration, one or more moisturizers may be used, such as glycerin or urea, in combination with one or more precursor agents for the biosynthesis of structural proteins, such as hydroxyproline, collagen peptides and the like.

By the way of example only, in case of slimming, at least one ketolytic agent or an alpha-hydroxyacid such a salicylic acid or 5-n-octanoicsalicylic acid may be used in combination with at least on liporegulating agent such as caffeine.

By way of example only, in the case of depigmentation, at least one keratolytic agent is used in combination with a depigmenting agent such as hydroquinone, tyrosinasee inhibitor (kosic acid), ascorbic acid, kojic acid and sodium metabisulfite an the like.

By way of example only, in the case of protection against free radical agents, vitamin E (against COO— radicals), superoxide dismutase (against $O_2$— free radicals) and sugar and caffeine (against OH— free radicals).

By way of example only, in the case of anti-aging, moisturizers, sunscreens, alpha-hydroxyacids, salicylic acid or surface restructuring agents may be used in combination with enzymes for the repair of DNA, vascular protective agents or phospholipids rich in oligoelements and polyunsaturated fatty acids.

By way of example only, in the case of anti-acne agents, keratolytics, such as salicylic acid, sulfur, lactic acid, glycolic, pyruvic acid, urea, resorcinol and N-acetylcysteine, and retinoids, such as retinoic acid and its derivatives may be used.

By way of example only, in the case of anti-inflammation, non-steroidal anti-inflammatory agents (NSAIDS) may be used, such as propionic acid derivatives, acetic acid, fenamic acid derivatives, biphenylcarboxylic acid derivatives, oxicams, including but not limited to aspirin, acetaminophen, ibuprofen, naproxen, benoxaprofen, flurbiprofen, fenbufen, ketoprofen, indoprofen, pirprofen, carporfen, and bucloxic acid and the like.

By way of example only, in the case of antibiotics and antimicrobials may be included in the composition of the invention. Antimicrobial drugs preferred for inclusion in compositions of the present invention include salts of—lactam drugs, quinolone drugs, ciprofloxacin, norfloxacin, tetracycline, erythromycin, amikacin, trilosan, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netlmicin, paromomycin, streptomycin, tobramycin, miconazole and amanfadine and the like.

By way of example only, in the case of sunscreen protection, suitable agents include 2-ethylhexyl p-methoxycinnamate, 2-ethylhexyl N,N-dimethyl-p-aminobenzoate, p-aminobenzoic acid, 2-phenyl p-methoxycinnamate, 2-ethylhexyl octocrylene, oxybenzone, homomenthyl salicylate, octyl salicylate, 4,4'-methoxy-t-butyldibenzoylmethen, 4-isopropyl dibenzoylmethane, 3-benzylidene camphor, 3-(4-methylbenzylidene) camphor, titanium dioxide, zinc oxide, silica, iron oxide, and mixtures thereof and the like. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema.

By way of example only, in the case of sunless tanning agents include, dihydroxyacetone, glyceraldehyde, indoles and their derivatives, and the like.

The composition may include cleansing surfactants. Cleansing surfactants are cationic, anionic, amphoteric or non-ionic surfactants which are water-soluble and produce a consumer-acceptable amount of foam. Nonionic surfactants are well-known materials and have been used in cleansing compositions. Therefore, suitable nonionic surfactants include, but are not limited to, compounds in the classes known as alkanolamides, block copolymers of ethylene and propylene, ethoxylated alcohols, ethoxylated alkylphenols, alkyl polyglycosides and mixtures thereof. In particular, the nonionic surfactant can be an ethoxylated alkylphenol, i.e., a condensation product of an alkylphenol having an alkyl group containing from about 6 to about 12 carbon atoms in either a straight chain or branched chain configuration with ethylene oxide, the ethylene oxide being present in an amount equal to at least about 8 moles ethylene oxide per mole of alkylphenol. Examples of compounds of this type include nonylphenol condensed with about 9.5 moles of ethylene oxide per mole of phenol; dodecylphenol condensed with about 12 moles of ethylene oxide per mole of phenol; dinonylphenol condensed with about 15 moles of ethylene oxide per mole of phenol; octylphenol condensed with about ten moles of ethylene oxide per mole of phenol; and diisooctyl phenol condensed with about 15 moles of ethylene oxide per mole of phenol.

A wide variety of acids, bases, buffers, and sequestrants can be utilized to adjust and/or maintain the pH and ionic strength of the compositions useful in the instant invention. Materials useful for adjusting and/or maintaining the pH and/or the ionic strength include sodium carbonate, sodium hydroxide, hydrochloric acid, phosphoric acid, sulfuric acid, acetic acid, sodium acetate, sodium hydrogen phosphate, sodium dihydrogen phosphate, citric acid, sodium citrate, sodium bicarbonate, triethanolamine, EDTA, disodium EDTA, tetrasodium EDTA, and the like.

The composition may be useful as a solubilization agent in cosmetic and personal care applications. A self-assembling system comprising the reversibly gelling composition exhibits thermogelation, pH sensitivity, and the ability to solubilize hydrophobic agents in aqueous media. When poloxamer is copolymerized with poly(acrylic acid) (PAA) according to the invention, the resulting composition is bioadhesive and can be applied in a number of therapies. The materials described in this invention combine "reverse" thermoviscosification mucoadhesion, solubilzation of hydrophobic and difficult to manage moieties, easy formulation, and protection of agents from degradation to provide a superior medium for cosmetic and personal care products.

The reversible viscosification of the composition at elevated temperatures makes the materials ideal for use as thickening agents in cosmetic and personal care products at any temperature above the transition. Another use of the "thickening" of solutions containing the composition as a thickener supplement in emulsions. Currently emulsifiers are often negatively effected by increased temperatures. An additive with reverse thermal viscosification properties, however, would react in exactly the opposite way, increasing its ability to emulsify as it gained three-dimensional structure upon heating above its transition temperature.

In the applications where the reversibly gelling polymer composition can act as a surfactant, the composition will have the ability to act as a primary emulsifier without any (or with very little) addition of traditional surfactant. The responsive composition will also act as a stabilizer for oil-soluble ingredients that would conventionally need to be solubilized by oils in formulation. The hydrophobic portion of the composition (PPO) forms domains which act as reservoirs for an oil-soluble or hydrophobic additive, such as an oil droplet, as is illustrated in FIG. 1. These two features of the material of the invention would enable it to be used as a base in a cosmetic formulation that would be non-greasy due to lack of oils, such as petrolatum and mineral oil. The increase in viscosity above the transition temperature adds structure and yield value to the water phase and results in a highly stable emulsion.

Thus, poloxamer:poly(acrylic acid) composition compositions are valuable materials in the formulation of cosmetic and personal care products. In particular, they may be useful as rheology modifiers, provide a cushioning effect on the skin, offer barrier properties and controlled release of actives. In addition, the polymer composition may serve as a surfactant and is compatible with most ingredients used in the cosmetic industry. The above properties of the poloxamer:poly(acrylic acid) composition provides a cosmetic composition that spreads evenly and smoothly and which leaves a lubricious feel to the skin.

A wide variety of acids, bases, buffers, and sequestrants can be utilized to adjust and/or maintain the pH and ionic strength of the compositions useful in the instant invention. Materials useful for adjusting and/or maintaining the pH and/or the ionic strength include sodium carbonate, sodium hydroxide, hydrochloric acid, phosphoric acid, sulfiric acid, acetic acid, sodium acetate, sodium hydrogen phosphate, sodium dihydrogen phosphate, citric acid, sodium citrate, sodium bicarbonate, triethanolamine, EDTA, disodium EDTA, tetrasodium EDTA, and the like.

The invention is described with reference to the following examples which are presented for the purpose of illustration only and are not limiting of the invention.

EXAMPLE 1

The example describes the synthesis of poloxamer:poly (acrylic acid) block copolymer.

A poloxamer was derivatized to obtain an acryloyl-terminated poloxamer according to the following equation.

$$\text{HO-EO}_{100}\text{PPO}_{65}\text{EO}_{100}\text{—OH}+2\text{H}_2\text{CCHC(O)} \\ \text{Cl}+\text{amine}\rightarrow\text{CH}_2\text{=CH—OO-} \\ \text{EO}_{100}\text{PPO}_{65}\text{EO}_{100}\text{—OOCH=CH}_2+\text{HCl} \quad (1)$$

Pluronic F127 (EO$_{100}$PPO$_{65}$EO$_{100}$; 30 g; BASF, Germany) was dissolved in dry toluene in a 250 mL round bottomed flask equipped with a magnetic stirrer and gas inlet-outlet to which 2.1 g triethylamine (Aldrich, 99+%) was added dropwise while stirring at 50° C. under nitrogen blanket. Then 1.2 mL of acryloyl chloride (Aldrich, 96%) was added dropwise into the flask, followed by addition of 0.75 mL triethylamine in 5 mL toluene under constant flow of nitrogen. The reaction mixture was stirred at 50° C. for 1.5 h and the contents were cooled to ambient temperature and filtered. All liquids were evaporated under vacuum and the resulting polymer flakes were redissolved in 200 mL toluene and precipitated by addition of hexane. The steps of dissolution and precipitation were repeated, and the polymer was finally dissolved in a minimum amount of methylene chloride and washed with excess hexane in a separation funnel. The polymer was then dried under vacuum (10$^{-3}$ Torr) at 20° C.

The acryloyl-modified poloxamer was then end-linked with poly(acrylic acid) by free radical polymerization according to eq (2).

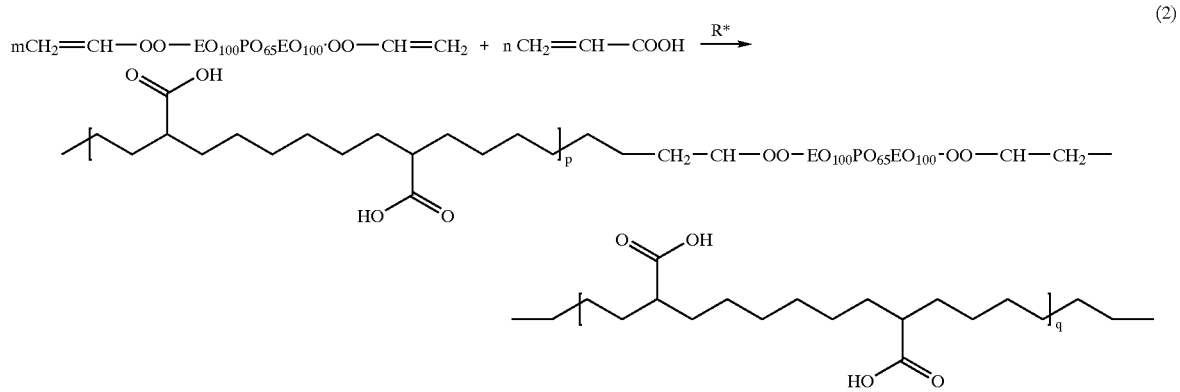

Acrylic acid (30 g, Aldrich, 99%) was neutralized by addition of 50 wt % aqueous NaOH solution while stirring. The degree of neutralization of acrylic acid was 6 mol %. Upon redissolution of precipitate, acryloyl-terminated poloxamer was charged into a flask and allowed to completely dissolve in acrylic acid under constant agitation. A 500 mL multi-necked, thermostated flanged glass reactor equipped with a mechanical stirrer, syringe sampler, thermometer, programmable heater bath, and a gas inlet/outlet was charged with 400 mL of poly(vinyl alcohol) (99% hydrolyzed, MW 13,000, Aldrich) solution in dodecane and was deoxygenated overnight by nitrogen flow while stirring. A freshly prepared initiator system comprising 5 mL of freshly prepared ammonium persulfate (Aldrich, 99.9+%; 300 mg) and N,N,N',N'-tetramethylethylenediamine (Aldrich, 99.5%; 0.1 mL) in water/acrylic acid mixture was added into the solution of poloxamer in acrylic acid while stirring. The resulting solution was immediately introduced into the reactor under nitrogen blanket while stirring. The reactor was allowed to equilibrate at ambient temperature, the nitrogen flow was discontinued and the slurry of the resulting polymer was filtered off using Whatman filter paper (retention 10 μm). The polymer was repeatedly washed with excess heptane and then with excess hexane in a separation funnel. The resultant white powder was dried under vacuum at 40° C. for 24 h.

The material was evaluated for thermal-responsiveness. The results are reported in FIG. 2.

EXAMPLE 2

The example describes the synthesis of poloxamer:poly (acrylic acid) block copolymer. The acryloyl-terminated poloxamer of Example 1 was end-linked with poly(acrylic acid) as follows.

Acrylic acid (40 g) was partially neutralized by addition of 50 w/w % aqueous NaOH solution while stirring. The degree of neutralization of acrylic acid was 6 mol %. Upon redissolution of precipitate, acryloyl-terminated poloxamer was charged into a flask and allowed to completely dissolve in acrylic acid under constant agitation. A 500 mL multi-necked, thermostated flanged glass reactor equipped with a mechanical stirrer, syringe sampler, thermometer, programmable heater bath, and a gas inlet/outlet was charged with 400 mL of 0.4% solution of poly(vinylpyrrolidinone-co-1-hexadecane) (International Specialty Products) in dodecane (Aldrich, 99%) and was deoxygenated overnight by nitrogen flow while stirring. A freshly prepared initiator system comprising a solution of lauryl peroxide (140 mg) and 2,2'-bisazo(2,4-dimethylpentanenitrile) (50 mg) in a small amount of acrylic acid was added into the solution of poloxamer in acrylic acid while stirring. The resulting solution was deoxygenated by nitrogen flow for 1 h and introduced into the reactor under nitrogen blanket while stirring. The reactor was equilibrated for 1 h while stirring at 20° C. under nitrogen purge introduced from the bottom of the reactor. Then at t=0, heating began and timing commenced.

The reactor was heated up to 70° C. at a rate of 1.5° C./min under constant nitrogen flow. At a certain temperature, exothermic reaction caused a rapid temperature increase inside the reactor. Then heat increase subsided and the reactor cooled to 70° C. and was maintained at this temperature for 8–10 h under stirring. The reactor was allowed to equilibrate at 20° C., the nitrogen flow was discontinued and the slurry of the resulting polymer was repeatedly washed with heptane and then with excess hexane in separation funnels. The resultant white powder was dried under vacuum at 40° C. for 24 h.

Size-exclusion chromatography (SEC) of the poloxamer-poly(acrylic acid) copolymers was run at various temperatures on a Shimadzu LC-10A Series high pressure liquid chromatograph (HPLC) set up with a Viscotek SEC$^3$ Tripole Detector System which included a laser scattering detector (scattering angle 90°; wavelength 670 nm; output power 126 mW; cell volume 12 μl), differential Wheatstone bridge viscometer (sensitivity 1×10⁻⁵ $\eta_{sp}$; shear rate 3000 s⁻¹; cell volume 50 μl), and a differential laser refractometer (wavelength 670 nm; sensitivity 3×10⁻⁸ Δn; shear rate 3000 s⁻¹; cell volume 8 μl). A 0.10–1.0 mg/mL sample of polymer solution was loaded onto a PL aquagel-OH mixed, 40, and 60 analytical temperature-controlled 3-column system (particle size 8 or 15 μm; dimensions 3×7.5 mm, Polymer Laboratories, Inc.) And then eluted using selected buffer. The SEC system was calibrated in the molecular weight (MW) range of 10³–10⁷ using poly(sodium acrylate) standards (American Polymer Standards Co.). For buffer preparation, ultrapure water from a Millipore Q purification system (conductivity less than 0.05 μS, outlet water filtered through a 0.22 μm filter) was used. Prior to use, polymer samples were dialyzed against excess buffer at 4° C. for 24 h with a Spectra/Por® cellulose ester membrane (molecular weight cut-off 500). For fractionation, PL aquagel-OH 40 and 60 preparative columns (particle size 10 μm; dimensions 300×25 mm) were used. Buffers contained 50 or 100 mM $Na_2HPO_4$ and varying concentrations of $NaNO_3$. pH was adjusted to 7.0 by addition of 1.0 M $H_3PO_4$, as needed. To achieve optimum reliability of the SEC measurements, the effect of the Donnan salt exclusion was studied by varying $NaNO_3$ concentrations. The area of the salt peaks was minimized when ionic strength of the buffer was 0.3 and 0.1 M for PAS and poloxamer-PAA samples, respectively. This observation agreed well with reported optimum salt concentrations for PAA standards. See, Kato et al., *Polymer* 25:218 (1984). Number-weight value for poloxamer-PAA was found to be 2.3×10⁶; z-average molar masses for poloxamer-PAA was found to be 2.9×10⁶; and α values for poloxamer-PAA was found to be 3.3×10⁶. Here, constants α and K are parameters of the Mark-Houwink equation ([η]×Km^α). See, Cooper A. R, in *Polymers: Polymer Characterization and Analysis*, J. I. Kroscyhwitz, Ed., Wiley, N.Y., 1990, p. 481.

The resulting copolymer was characterized by NMR and IR as follows.

¹H-NMR (D₂O, 20° C., 10%): δ 3.7 (m, methylene HC—OC), 3.51 (m, methylene, HC—OC), 2.55, 2.15 (m, methine, HC—COONa), 1.55 (m, methylene, HC—C—COONa), 1.1.6 (s, CH₃ in PPO).

IR (KBR): 1740 (COONa and COOH), 1100 cm⁻¹ (COC).

Figure 3A:
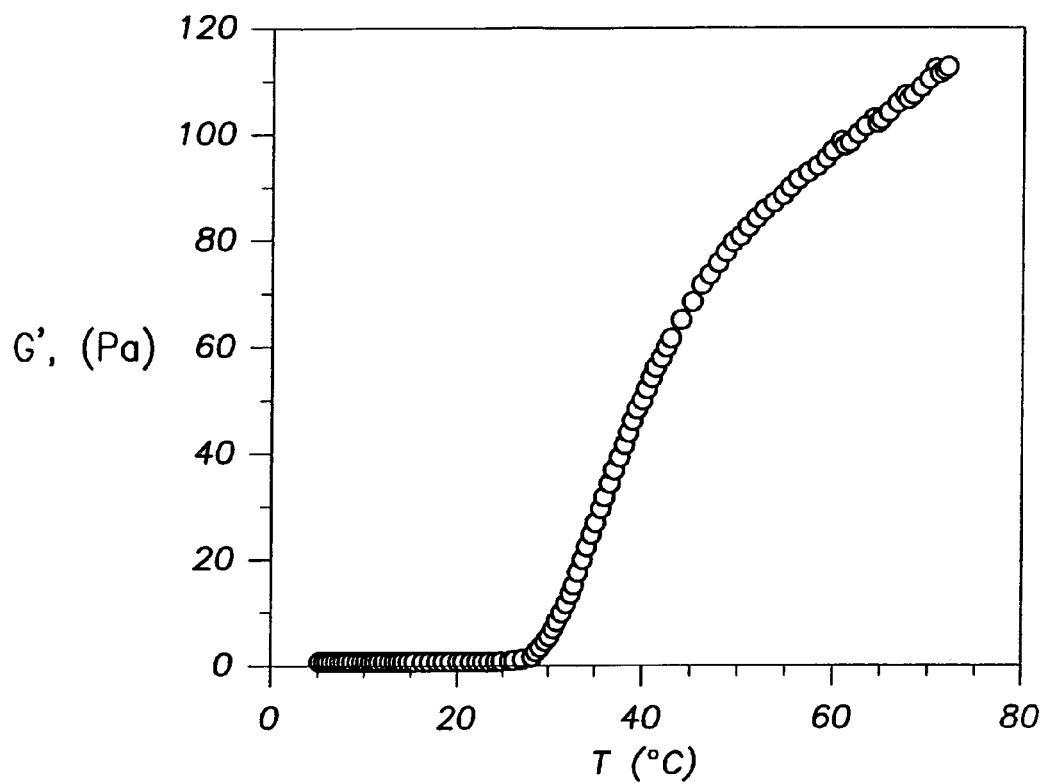
FIG. 3 is a graph of G' vs. temperature (3A) and G" vs. temperature (3B) for a 2 wt % poloxamer/poly(acrylic acid) (1:1) aqueous composition demonstrating reversibility of the viscosity response.
Figure 3B:
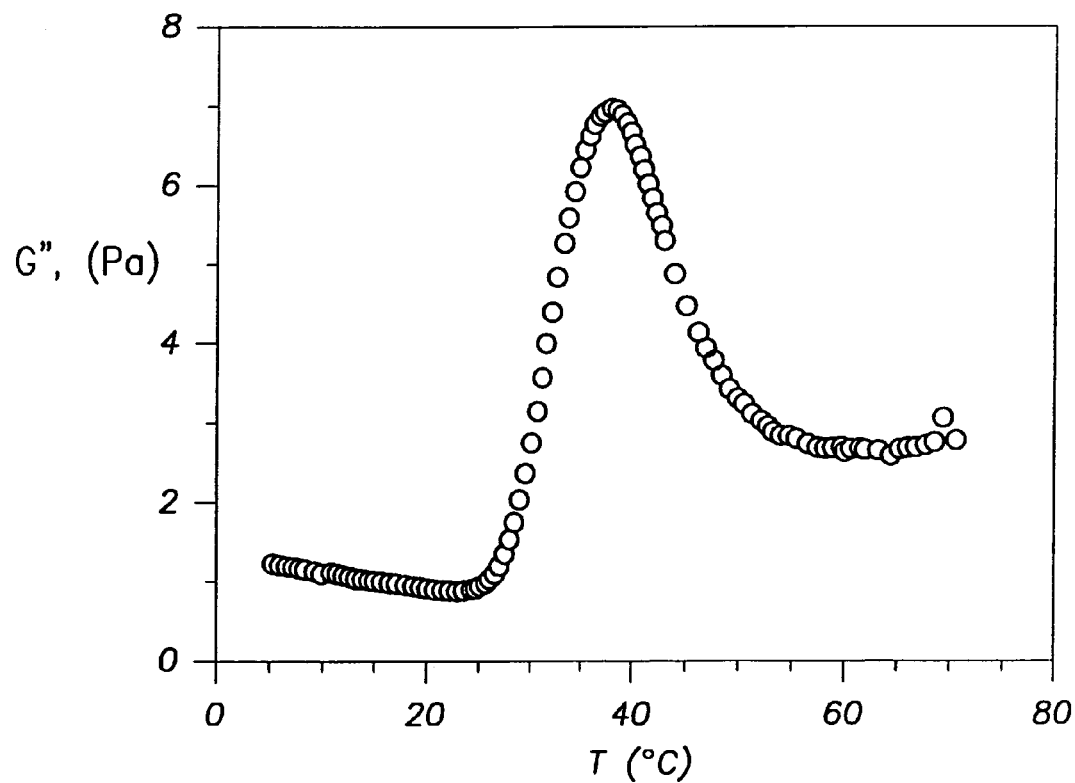

Aggregation of the poloxamer-PAA polymer in 1% aqueous solution (pH 7.0) is illustrated in FIG. 3, in which FIG. 3A displays the change of storage modulus G' with temperature and FIG. 3B shows the change of loss modulus G" with temperature. The storage modulus of the solution increases with temperature indicating transition from Newtonian-like liquid to a gel with significant elastic modulus.

Figure 4:
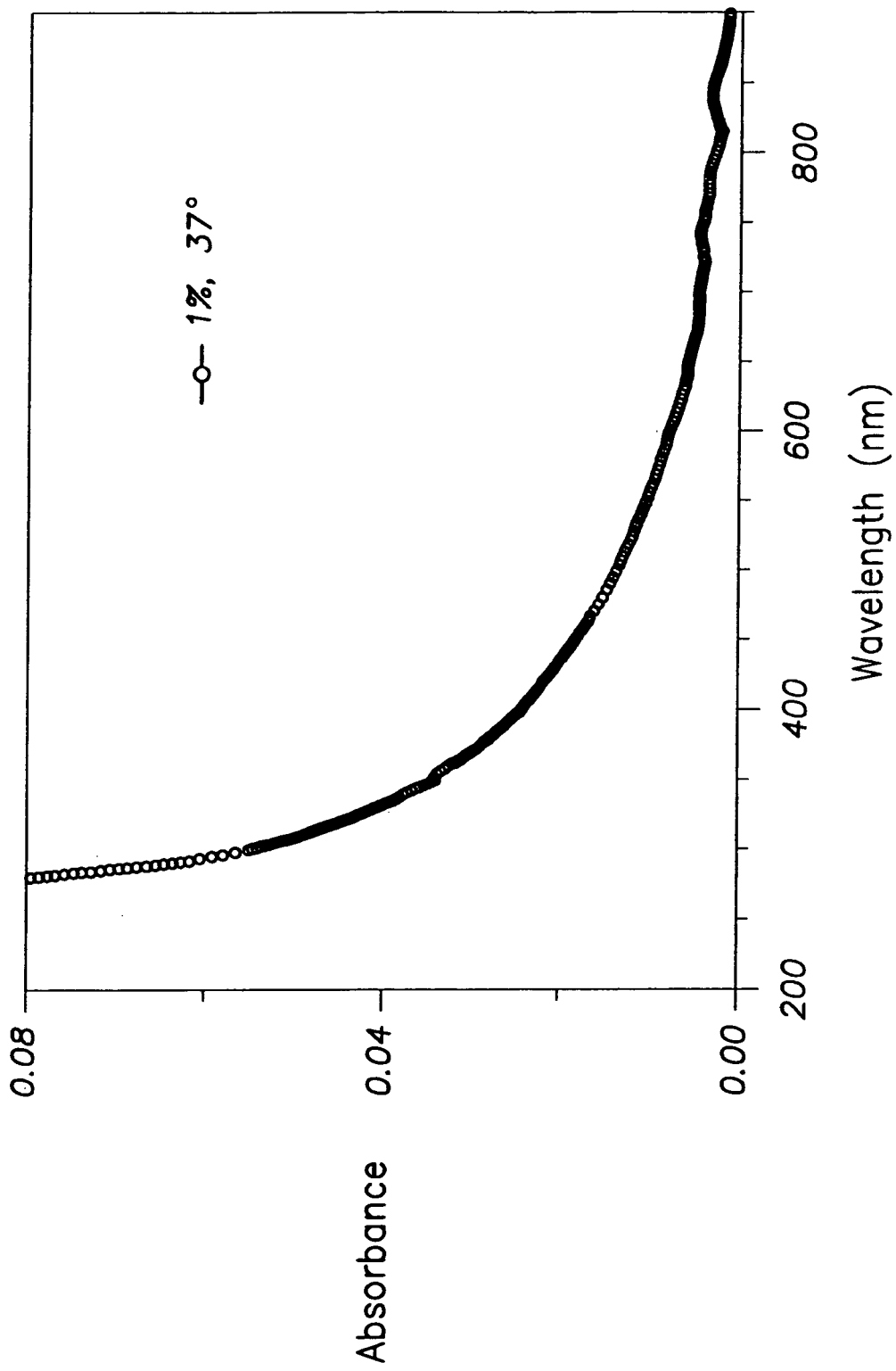
FIG. 4 is a electronic spectrum of a 1 wt % poloxamer/poly(acrylic acid) (1:1) aqueous composition indicating translucence in the visible range.

An electronic spectrum of the 1% poloxamer-PAA sample (measured using a Shimadzu 1601 PC UV-vis spectrophotometer equipped with a thermostated quartz cell with a 1 cm path length) is shown in FIG. 4. The solution shows electronic absorbence at 37° C. below 0.04 in the visible range and this is completely translucent to the human eye.

EXAMPLE 3

This example illustrates the method of synthesis of N-acryloyl-terminated poloxamer according to the following equation (3) and the formation of a poloxamer-PAA copolymer therefrom.

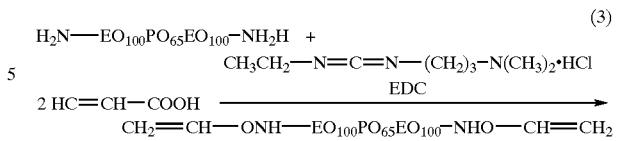

Amino-terminated poloxamer was synthesized as described by Chen et al. In "Temperature-Induced Gelation Pluronic-g-poly(acrylic acid) Graft Copolymers for Prolonged Drug Delivery to the Eye" in *Poly(ethylene glycol) Chemistry and Biological Applications*, (J. M. Harris and S. Zalipski, Eds. ASC Symp. Ser 680, 12997 pp441–457), except that Pluronic F127 NF was used and both ends of the Pluronic oligomer were functionalized. Then conjugation of acrylic acid and amino-terminated Pluronic F127 NF was accomplished by simultaneous activation and coupling with a water-soluble condensing agent, 1-ethyl-3-(3-dimethylaminopropyl)carbodiimide (EDC), as shown in eq. (3). The amino-terminated poloxamer and EDC components were dissolved at concentrations of 10 mg/mL, and 2 mg/mL in 10 mM phosphate buffer (pH 7.4) at 4° C. The mixture was then gently shaken for 24 h at 4° C. The reaction mixture was then dialyzed against excess deionized water at 4° C. for 48 h using Spectra/Pol® cellulose ester membrane (MW cut-off 55, Spectrum®, Laguna Hills, Calif.) and passed through a PL-SCX semi-preparative cation-exchange column (1000 Å, 8 μm, 100×10 mm, Polymer Laboratories, Inc. Amherst, Mass.) at a flow rate of 0.5 mL/min with 10 mM phosphate buffer as an eluent. The fraction absorbence was monitored at 215 nm. The resulting polymer was dried under high vacuum (10⁻⁵ Torr( at 30° C.

The resulting polymer had a characteristic vinyl stretch at 1640 cm⁻¹ in FTIR spectrum and UV maximum at λ215 nm was observed in the electronic spectrum. As a control, a mixture of amino-activated Pluronic F127 NF and acrylic acid mer was run without addition of the EDC activation reagent After the same treatment as above, no UV maximum at λ215 nm was observed.

The thus obtained acryloyl-terminated poloxamer was end-linked with poly(acrylic acid) as follows. Acryloyl-terminated poloxamer (3 g) was dissolved in acrylic acid (99%, Aldrich; 5 g) and the solution was charged into a 100-mL multinecked, thermostated flanged glass reactor equipped with a mechanical stirrer, syringe sampler, thermometer, programmable heater bath, and a gas inlet/outlet. The reactor was charged with 30 mL of 1% poly(vinyl alcohol) (99% hydrolyzed, MW 13,000, Aldrich) solution in dodecane and was deoxygenated for 2 h by nitrogen flow while stirring. A freshly prepared initiator system comprising 1 mL of freshly prepared ammonium persulfate (Aldrich, 99.9+%; 10 mg) and N,N,N',N'-tetramethylethylenediamine (Aldrich, 99.5%; 0.02 mL) in water/acrylic acid mixture was added into the solution of poloxamer in acrylic acid while stirring. The solution was equilibrated for 24 h at 4° C. under nitrogen purge introduced from the bottom of the reactor. The reactor was allowed to equilibrate at ambient temperature, the nitrogen flow was discontinued and the slurry of the resulting polymer was filtered off using Whatman filter paper (retention 10 μm). The polymer was repeatedly washed with excess heptane and then with excess hexane in a separation funnel. The resultant white powder was dried under vacuum at 40° C. for 24 h.

The resulting copolymer was characterized by NMR and IR as follows.

$^{13}$C-NMR (D$_2$O, 20° C., 10%): δ 183 (ester COOH) 156 (urethane) 76–70 (ether COC) 46–37 (primary C—O and secondary C—C), 17.9 (CH$_3$ of PPO).

IR (KBR): 2939 (methyl CH of PPO), 1685 (C=O), 1220 (ester C—O stretch), 1099(antisym and sym COC stretch) cm$^{-1}$.

Figure 5:
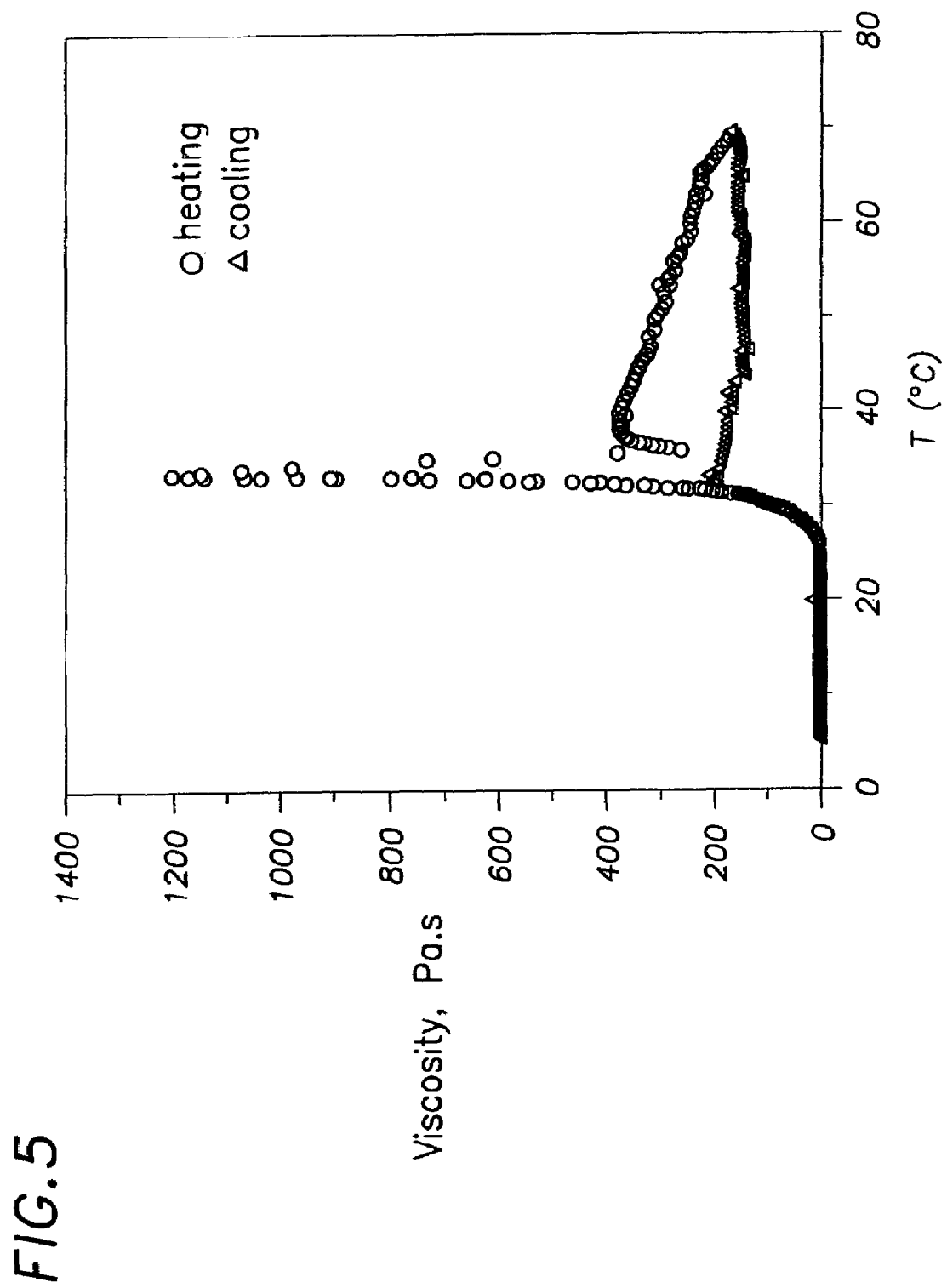
FIG. 5 is a graph of viscosity vs. temperature for a 2 wt % poloxamer/poly(acrylic acid) (1:1) aqueous composition.

The material was evaluated for thermal-responsiveness. The results are reported in FIG. 5. Viscosity in equilibrium flow experiments of a 2% aqueous solution (pH 7.0) indicates that the solution viscosity at body temperature. The viscous gels were sheared by the applied stresses.

EXAMPLE 5

The synthesis of poly(oxyethylene-co-oxypropylene-co-oxyethylene) diacrylate is described.

The following steps are carried out using the procedures described previously in Example 1. Pluronic F127 NF (30.0 g) is dissolved in dry toluene (250 mL) and heated to 50° C. in a round-bottom flask equipped with magnetic stirrer and a gas inlet-outlet. Triethylamine (2.1 g) is added dropwise while stirring at 50° C. under nitrogen blanket. Acryloyl chloride (1.2 mL) is added dropwise into the reaction flask.

In a separate container triethylamine (0.75 mL) is dissolved in toluene (5 mL) and added dropwise to the reaction flask under constant flow of nitrogen. The reaction mixture is stirred at 50° C. for 1.5 h. The reaction vessel is cooled to ambient temperature (25° C.). When it reaches ambient temperature the solution is filtered. The solids are discarded. This solution is added slowly to hexane (1,250 mL) and the polymer is precipitated. The procedure of redissolution and precipitation was repeated. The resulting polymer is repeatedly dissolved in minimum amount of methylene chloride and washed with excess hexane in separation funnel. The polymer is then dried under vacuum at 20° C.

EXAMPLE 6

This example describes the synthesis of copolymers of modified Pluronic F127 poloxamer and poly(acrylic acid). The poloxamer is end-activated with sulfhydryl functionality which serves as a chain-transfer agent for polymerization of acrylic acid, followed by conjugation of the poloxamer and polymerized acrylic acid.

2,4-dinitrophenylacetic acid was synthesized as follows. Mercaptoacetic acid (97%, Aldrich, 5 g, 54 mol) was added dropwise to 50 mL of a solution of 2,4-dinitrofluorobenzene (Sanger's Reagent, 99%, Aldrich, 10 g, 54 mmol) and triethylamine (99+%, Aldrich, 10 g, 99 mmol) in dry chloroform in a three-necked flask equipped with magnet stirrer and nitrogen inlet-outlet. The reactor was stirred overnight under nitrogen blanket. The color of the solution changed from orange to dark red. The solution was extracted with 1M HCl and repeatedly with water. The organic phase was separated and filtered to yield yellow crystals which were repeatedly recrystallized from chloroform. Yield was 91%, $M_p$ 170.5° C. and was characterized by $_1$H-NMR.

The Poloxamer was then treated with the protected thiol to obtain the end-activated compound shown in equation (4).

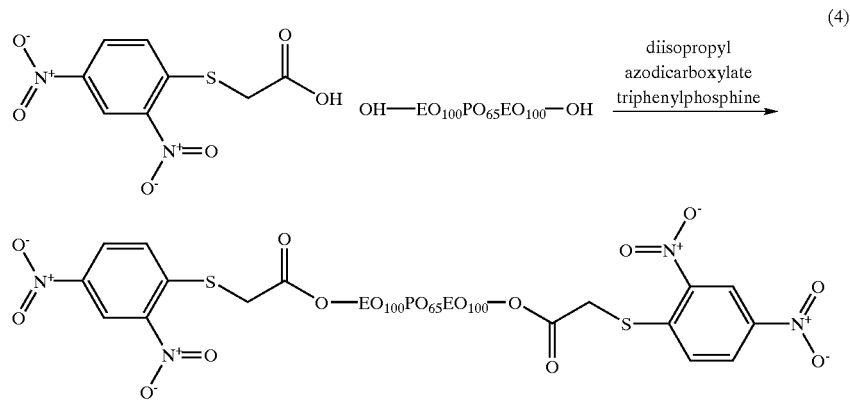

(4)

Diisopropyl azodicarboxylate (95%, Aldrich, 5 g, 25 mmol) was added to a stirred solution of Pluronic F127 NF (54.4 g, 8 meq OH groups) and triphenylphosphine (99%, Aldrich, 6.5 g, 25 mmol) in 30 mL of dry tetrahydrofuran (THF). Prior to use, the poloxamer was lyophilized to remove water traces. The solution was then stirred for 48 h at ambient temperature under a nitrogen blanket. Then the Solution was precipitated into chilled methanol/hexane (2:1), dried, redissolved in THF and repeatedly precipitated by hexane. After filtering and drying under vacuum, the yield 88%.

The protected-thiol functionalized poloxamer was then deprotected to obtain the reactive thiol according to equation (5).

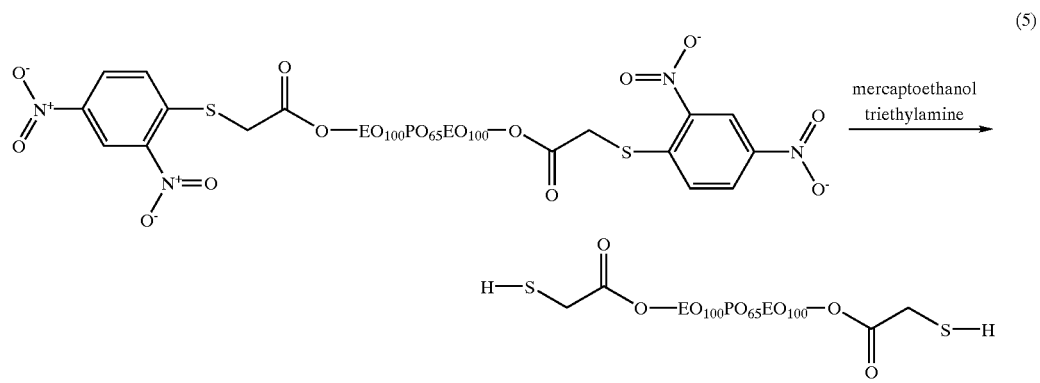

(5)

Poloxamer functionalized with protected thiol (20 g) was dissolved in dry THF (100 mL) and 2-mercaptoethanol (98%, Aldrich, 5 g) Triethylamine (10 g) was added to the solution dropwise and the mixture was stirred at ambient temperature for 16 h. The resulting mixture was precipitated into chilled methanol/hexane (2:1), dried, redissolved in THF and repeatedly precipitated by hexane. After filtering and drying of the resulting polymer under vacuum, the yield was 90%.

The thiol-functionalized poloxamer of the preceding step was then dissolved in acrylic acid (99%. Aldrich, 5 g) and the solution was charged into a 100 mL multinecked, thermostated flanged glass reactor equipped with a mechanical stirrer, syringe sampler, thermometer, programmable heater bath, and a gas inlet/outlet. The reactor was charged with 50 mL of 1% poly(vinyl alcohol) (99% hydrolyzed, MW 13,000, Aldrich) solution in dodecane and was deoxygenated for 2 h by nitrogen flow while stirring. A freshly prepared initiator system comprising 1 mL of freshly prepared ammonium persulfate (Aldrich, 99.9+%; 30 mg) and N,N,N',N'-tetramethylethylenediamine (Aldrich, 99.5%; 0.2 mL)in water/acrylic acid mixture was added into the solution of poloxamer in acrylic acid while stirring. The solution leas equilibrated for 24 h at 30° C. under nitrogen purge introduced from the bottom of the reactor. The reactor was allowed to equilibrate at ambient temperature, the nitrogen flow was discontinued and the slurry of the resulting polymer was filtered off using Whatman filter paper (retention 10 $\mu$m). The polymer was repeatedly washed with excess heptane and then with excess hexane in a separation funnel. The resultant white powder (poloxamer end-modified with poly(acrylic acid)) was dried under vacuum at 40° C. for 24 h.

The resulting copolymer was characterized by NMR and IR as follows.

$^{13}$C-NMR (D$_2$O, 20° C., 10%): δ 177 (ester COOH), 76–70 (ether C—O—C), 66 (C—S), 46–37 (primary C—O and secondary C—C), 17.9 (CH3of PPO).

IR (KBR): 2945 (methyl CH of PPO), 1743 (C═O), 1220 (ester C—O stretch), 1099(antisym and sym COC stretch) cm$^{-1}$.

Gel-permeation chromatography was run as described in Example 2. Number-weight, z-average molar masses for the copolymer were found to be 1.30×10$^5$, 1.35×10$^5$ and 1.39×10$^5$, respectively. The very narrow molecular weight distribution agrees well with the chain-transfer mechanism of polymerization which is shown in Scheme 1.

Scheme 1
Telomerization of acrylic acid using
thiol-functionalized Pluronic as a chain-
transfer agent

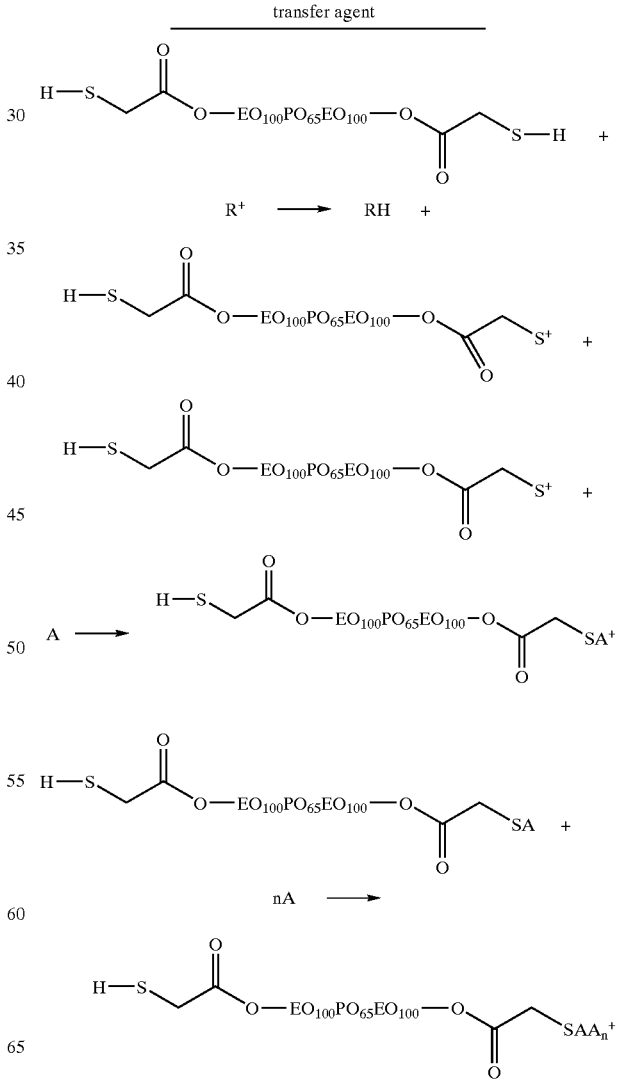

-continued

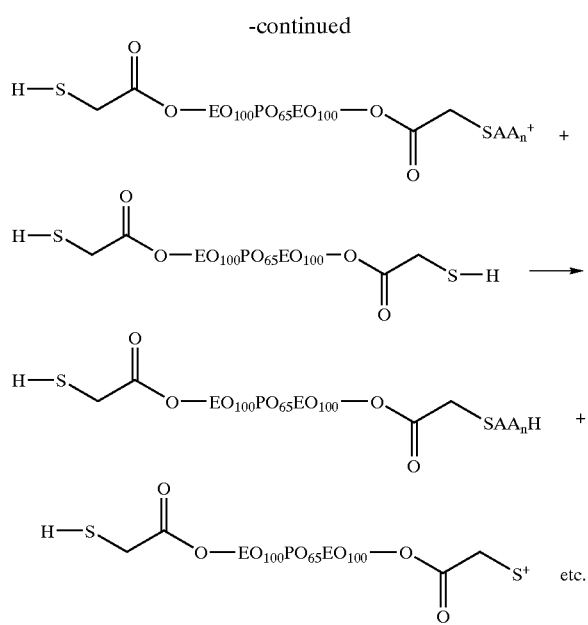

Figure 6:
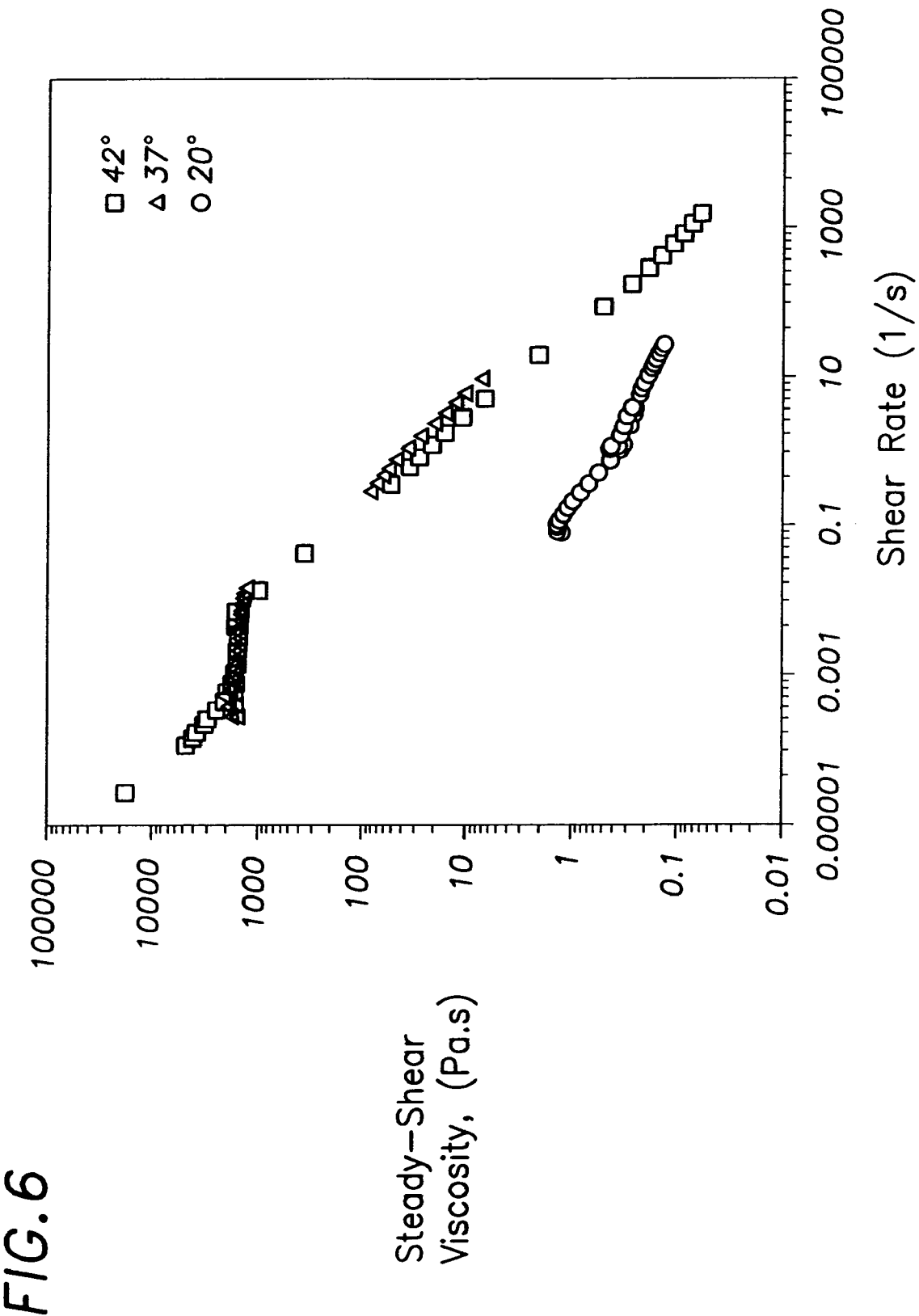
FIG. 6 is graph of steady state viscosity vs. shear rate for an 8 wt % poloxamer/poly(acrylic acid) (1:1) aqueous composition at various temperatures.

The material was evaluated for thermal-responsiveness. The results are reported in FIG. 6. Viscosity in equilibrium flow experiments of an 8% aqueous solution (pH 7.0) indicates that the solution viscosify at body temperature. The steady-shear viscosity that is higher by many orders of magnitude at body temperature than at ambient confirms the gelation process.

EXAMPLE 7

The following examples provide exemplary formulations for the pharmaceutical and cosmetic applications of the invention.

Aceclofenac Gel (1.5%). An example of a gel containing Aceclofenac as the active agent.

| | |
|---|---|
| Aceclofenac | 1.5 g |
| Miglyol ® 812 (Dynamit-Nobel) | 9.9 g |
| Water | qs |
| Hydrogel of the invention | 3.0 g |

Mix the Aceclofenc and Miglyol with water and cool to about 5° C. Add slowly Hydrogel and continue stirring until the hydrogel is dissolved. Maintain cooling until the air bubbles escape. A milky gel is obtained. When heated to body temperature the gel firms.

Lidocain Gel (2%). An example of a topical gel containing Lidocaine as the active agent.

| | |
|---|---|
| Lidocain hydrochloride | 2 g |
| Water | 58 g |
| Propylene glycol | 20 g |
| Hydrogel of the invention, solution 10% w/w | 20 g |

Prepare solution of Lidocain and propylene glycol in water at room temperature, cool to about 5° C. and add slowly Hydrogel solution to the well-stirred solution until it is homogenized. Maintain the temperature until the air bubbles escaped. A clear colorless gel is obtained. The product is liquid at room temperature and becomes firm gel at body temperature to allow precise application and residence.

Carbonate Dry Syrup (12.5% +12.5%) (Aluminum Hydroxide+Magnesium). An example of anti-acid esophageal preparation is provided. Granulate the following ingredients.

| | |
|---|---|
| Aluminum hydroxide dry gel | 25.0 g |
| Basic Magnesium carbonate | 25.0 g |
| Kollidon CL-M | 29.0 g |
| Sorbitol, crystalline | 25.6 g |
| Orange flavor | 5.0 g |

Prepare the following solution:

| | |
|---|---|
| Kollidon 30 | 10.0 g |
| Coconut flavor | 0.4 g |
| Banana flavor | 0.5 g |
| Saccharin sodium | 0.5 g |
| Water | 0.1 g |

Mix the granulates with the solution and pass through a sieve and air dry. Shake 60 g of the resulting powder with 100 ml of water containing 3 wt % inventive Hydrogel. This solution will coat the esophagus to provide relief from GERD.

Diltiazem Tablets. An example for sustained release tablet.

| | |
|---|---|
| Diltiazem | 60 g |
| Ludipress (BASF) | 130 g |
| Polyethylene glycol 6000 | 5 g |
| Aerosil 200 | 1 g |
| Magnesium stearate | 1 g |
| Hydrogel of the invention, powder | 10 g |

Mix all components, pass through a sieve and press with low compression force. This tablet will have a sustain release characteristics due to the slow dissolution of the Hydrogel at body temperature.

Beta Carotene Effervescent Tablets. An example for sustained release effervescent tablet.

| | |
|---|---|
| Lucarotin ® powder (BASF) | 70 g |
| Ludipress | 113 g |
| Citric acid, anhydrous | 200 g |
| Sodium bicarbonate | 120 g |
| Sodium carbonate | 12 g |
| Sodium cyclamate | 20 g |
| Aspartame | 15 g |
| Orange flavor | 20 g |
| Polyethylene glycol 6000, powder | 20 g |
| Hydrogel of the invention, powder | 10 g |

Pass all components through o 0.8 mm sieve, mix and press with medium or high compression force at maximum 30% of relative atmospheric humidity.

Chlorohexidine Gel (2%). A formulation to be used in the oral cavity with longer residence time

| | |
|---|---|
| Chlorhexidin diacetate | 2 g |
| 1,2-Propylene glycol | 30 g |
| Hydrogel of the invention, powder | 2 g |
| Pluronic F127, powder | 2 g |
| Water | qs |

Dissolve chlorhexidin diacetate in propylene glycol at >70° C., add water under stirring. Cool to about 5° C. and add the inventive Hydrogel and F127. Stir until dissolved. Maintain the temperature until the air bubbles escaped. A clear colorless gel is obtained.

Aloe Vera Gel. An example for a cosmetic formulation.

| | |
|---|---|
| Aloe vera extract | 0.4 g |
| Propylene glycol | 5.0 g |
| Preservative | q.s. |
| Water | 73.6 g |
| Cremophor RH 40 [1] | 1.1 g |
| Perfume | q.s. |
| Hydrogel of the invention, powder | 3.0 g |

Prepare the solutions containing all ingredients but the responsive Hydrogel. Cool this mixture to about 5° C. and dissolve the inventive Hydrogel. Maintain the temperature until the air bubbles escaped. The formed hydrogel is clear and flowable at room temperature. Once applied on the skin the solution viscosity to provide a cushion and lubricous effect.

Hydrocortisone Aqueous Gels (1%). Hydrophobic substances is solubilized by Hydrogel of the invention.

| | |
|---|---|
| Hydrocortisone acetate | 1.0 g |
| Hydrogel of the invention | 4.0 g |
| Carbopol 940 (Goodrich) | 0.5 g |
| Water | qs |
| Preservative | q.s. |
| Triethanolamine 10% soluton | 8 g |

Dissolve the inventive hydrogel in cold water (5° C.). Add the Carbpol, and mix until the solution is clear. Suspend the hydrocortisone and allow it to dissolve at room temperature, under gentle stirring overnight. Add a solution of triethanolamine and continue to stir until the gel is clear.

Metronidazol Vaginal Gel (1.2%). An example for a vaginal formulation.

| | |
|---|---|
| Metronidazol | 1.2 g |
| Pluronic F 127 | 2.0 g |
| Hydrogel of the invention | 3.0 g |
| Water | qs g |

Mix all the above ingredients at 5° C. until dissolved. Maintain the temperature until the air bubbles disappeared.

Vitamin E Gel-Cream (10%). An example for a cosmoceutical formulation of a semi-solid gel.

| | |
|---|---|
| Vitamin E acetate (BASF) | 10 g |
| Propylene glycol | 15 g |

-continued

| | |
|---|---|
| Hydrogel of the invention | 5 g |
| Pluronic F127 | 3 g |
| Water | qs |

Mix vitamin E acetate with propylene glycol and add the water. After cooling to about 5° C. dissolve slowly the Hydrogel in the well stirred mixture. Maintain cool until the air bubbles escaped. The inventive Hydrogel provide a solublizier for the Vitamin E and provides the "body" of the formulation.

What is claimed is:

1. A reverse thermally viscosifying composition comprising:
   a block copolymer in an aqueous medium, the block copolymer comprising,
   a first polyoxyalkylene block having a hydrophobic region and a hydrophilic region, said polyoxyalkylene block forming micelles in solution in response to a change in temperature, and
   at least a second block comprising a bioadhesive polymer or oligomer,
   wherein the composition reversibly viscosifies at a temperature in the range of about 22° C. to about 40° C.

2. A pharmaceutical composition, comprising:
   a reverse thermally viscosifying composition comprising,
   a block copolymer having first and second blocks in an aqueous medium, wherein the first block comprises a polyoxyalkylene having a hydrophobic region and a hydrophilic region; said polyoxyalkylene block forming micelles in solution in response to a change in temperature, and the second block comprises a bioadhesive polymer or oligomer; and
   an active agent which imparts a pharmaceutic or cosmetic effect, said composition characterized in that it viscosifies at a temperature in the range of about 22° C. to about 40° C.

3. The composition of claim 1 or 2, wherein the hydrophobic region of the polyoxyalkylene comprises polyoxyethylene and the hydrophilic region of the polyoxyalkylene comprises polyoxypropylene.

4. The composition of claim 1 or 2, wherein the bioadhesive polymer or oligomer is a mucoadhesive.

5. The composition of claim 1 or 2, wherein the bioadhesive polymer or oligomer comprises a poly(vinylcarboxylic acid).

6. The composition of claim 5, wherein the poly(vinylcarboxylic acid) is selected from the group consisting of acrylic acid, substituted acrylic acid, methacrylic acid, substituted methacrylic acids, acids, and ionized forms thereof.

7. The composition of claim 1 or 2, wherein the polyoxyalkylene comprises a triblock polymer of polyoxyethylene (POE) and polyoxypropylene (POP) having the formula $(POP)_a (POE)_b (POP)_a$, where a is in the range of 100–50 and b is in the range of 50–70.

8. The composition of claim 1 or 2, wherein the aqueous medium is selected from the group consisting of water, salt solutions and water with water-miscible organic compound(s).

9. The composition of claim 1 or 2, wherein the viscosification occurs at a temperature in the range of about 30° C. to about 37° C.

10. The composition of claim 1 or 2, wherein the block copolymer is present in an amount in the range of about 0.01 to 20 wt % of the total composition.

11. The composition of claim 1 or 2, wherein the block copolymer is present in an amount in the range of about 0.1 to 10 wt % of the total composition.

12. The composition of claim 1 or 2, wherein the block copolymer is present in an amount in the range of about 0.01–1 wt % of total composition.

13. The composition of claim 2, wherein the pharmaceutically active agent is selected from the group consisting of anti-ulcer agents, sucralfate, H2-blocking agents, antipyretics, analgesics, antacids, antiflatulents, anticonvulsants, antidiarrheals, antifungals, anihypertensives, antihistimines, antiprutitics, antiinfectives, antinauseants, antireflux agents, antispasmodics, contraceptives, hormonals, steroids, cough/cold remedies, diuretics, laxatives, tranquilizers, muscle relaxants, mineral supplements, sedatives, vitamins and mixtures thereof.

14. The composition of claim 2, wherein the pharmaceutical agent is absorbable through skin or mucosal membranes.

15. The composition of claim 2, wherein the pharmaceutical agent is absorbable through vaginal mucosal membrane.

16. The composition of claim 15, wherein the pharmaceutically active agent is selected from the group consisting of natural and synthetic hormones, anti-fungals, contraceptives, anti-yeast agents, steroids, moisturizers, spermicides, anti-virals, analgesics and anaesthetics.

17. The composition of claim 2, wherein the pharmaceutical agent is absorbable through nasal mucosal membrane.

18. The composition of claim 17, wherein the pharmaceutically active agent is selected from the group consisting of decongestants, antihistamines, anti-osteoporosis agents, hormones, antineoplastic agents, Parkinsonism drugs and vaccines.

19. The composition of claim 2, wherein the pharmaceutical agent is absorbable through rectal mucosal membrane.

20. The composition of claim 2, wherein the pharmaceutical agent is absorbable through otic mucosal membrane.

21. The composition of claim 20, wherein the pharmaceutically active agent is selected from the group consisting of miotics, sympathomimetrics, beta-blockers, prostaglandin, muscarinic antagonists, anti-infectives and carbonic anhydrase inhibitors.

22. The composition of claim 2, wherein the pharmaceutical agent is absorbable through ophthalmic mucosal membrane.

23. The composition of claim 2, wherein the pharmaceutical agent is absorbable through esophageal mucosal membrane.

24. The composition of claim 2, wherein the pharmaceutical agent is absorbable through oral cavity membrane.

25. The composition of claim 2, further comprising an additive selected from the group consisting of antioxidants, isotonizing agents, buffer, flavoring and preservatives.

26. The composition of claim 2, wherein the pharmaceutical composition is applied in the form of drops or spray.

27. The composition of claim 2, wherein the composition is incorporated into a tablet for oral administration.

28. The composition of claim 2, wherein the composition is injectible.

29. The composition of claim 1 or 2, wherein the polyoxyalkylene comprises a triblock polymer of polyoxyethylene (POE) and polyoxypropylene (POP) having the formula $(POE)_a(POP)_b(POE)_c$, where a is about 100 and b is about 65.

* * * * *